United States Patent
Urano et al.

(10) Patent No.: US 7,436,928 B2
(45) Date of Patent: Oct. 14, 2008

(54) RADIOTHERAPY DEVICE CONTROL APPARATUS AND RADIATION IRRADIATION METHOD

(75) Inventors: Susumu Urano, Hiroshima (JP); Shuji Kaneko, Hiroshima (JP); Masahiro Yamada, Hiroshima (JP); Noriyuki Kawada, Hiroshima (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 11/707,069

(22) Filed: Feb. 16, 2007

(65) Prior Publication Data
US 2007/0297566 A1    Dec. 27, 2007

(30) Foreign Application Priority Data
Jun. 23, 2006    (JP)    ............................. 2006-174287

(51) Int. Cl.
*A61N 5/10*    (2006.01)
(52) U.S. Cl. .......................................... 378/65; 378/64
(58) Field of Classification Search .............. 378/64–69
See application file for complete search history.

(56) References Cited

U.S. PATENT DOCUMENTS

| | | | |
|---|---|---|---|
| 5,673,300 | A | 9/1997 | Reckwerdt et al. |
| 6,307,914 | B1 * | 10/2001 | Kunieda et al. ............... 378/65 |
| 6,915,003 | B2 | 7/2005 | Oosawa |
| 7,035,445 | B2 | 4/2006 | Oosawa |
| 2005/0111621 | A1 * | 5/2005 | Riker et al. ................... 378/65 |
| 2005/0201516 | A1 * | 9/2005 | Ruchala et al. ............... 378/65 |

FOREIGN PATENT DOCUMENTS

| | | |
|---|---|---|
| JP | 10-099456 | 4/1998 |
| JP | 2001-291087 | 10/2001 |

(Continued)

OTHER PUBLICATIONS

Japanese Office Action issued for Japanese application No. JP 2006-174287. [With English language translation attached thereto.].

*Primary Examiner*—Hoon Song
(74) *Attorney, Agent, or Firm*—Wenderoth, Lind & Ponack, L.L.P.

(57) ABSTRACT

A radiotherapy device control apparatus includes: a template matching section; an affected area position calculating section; and an irradiation position control section. The radiotherapy device control apparatus controls a radiotherapy device. The radiotherapy device includes: a therapeutic radiation irradiation device radiating therapeutic radiation, and an imager generating an imager image of a subject by using radiation transmitted through the subject. The template matching section calculates degree of coincidence when a pattern matching is executed on the imager image with a plurality of image templates in which positional relations between an object area and a non-object area of the subject are different, and selects a specified image template having the degree of coincidence within a predetermined range from the plurality of image templates. The affected area position calculating section calculates a position of the object area by using the specified image template. The irradiation position control section judges whether a relative position of the object area with respect to the therapeutic radiation irradiation device. The irradiation position control section moves one of the therapeutic radiation irradiation device and a couch with the subject by using a drive device provided with the radiotherapy device such that the object area is irradiated with the therapeutic radiation.

48 Claims, 11 Drawing Sheets

FOREIGN PATENT DOCUMENTS

| | | |
|---|---|---|
| JP | 2001-325584 | 11/2001 |
| JP | 2002-032735 | 1/2002 |
| JP | 2006-501922 | 1/2006 |
| JP | 2006-051199 | 2/2006 |
| WO | 2004/034329 | 4/2004 |

* cited by examiner

RADIOTHERAPY DEVICE CONTROL APPARATUS AND RADIATION IRRADIATION METHOD

BACKGROUND OF THE INVENTION

1. Field of the Invention

The present invention relates to a radiotherapy device control apparatus and a radiation irradiation method, and more specifically to a radiotherapy device control apparatus and a radiation irradiation method for use in treating a patient by irradiating his or her affected area with radiation.

2. Description of the Related Art

Radiotherapy is known which treats a patient by irradiating his or her affected area (tumor) with radiation. It is desired that the radiotherapy provides a high therapeutic effect and that a dosage of radiation thereof irradiated to normal cells be smaller than a dosage of radiation irradiated to cells at the affected area.

The radiotherapy device is proposed which tracks a position of an affected area based on transmitted images photographed by applying diagnostic X-rays, and irradiates the position with a radiation for treatment. However, to achieve therapy with a high accuracy and reliability, it is desired that accuracy for detecting position of the moving affected area be improved.

Japanese Laid-Open Patent Application JP2001-291087A discloses an image aligning method (method and device for positioning image) capable of aligning two images flexibly depending on state of alignment or adaptively depending on characteristics of a subject. The image aligning method is a method of aligning two images of the same subject to be compared. According to the image aligning method, by setting at least a pair of interest regions and performing local matching between interest regions of each pair, positional relationship between the interest regions is automatically obtained. In addition, the alignment state between the interest regions is visually displayed and interest regions requiring realignment are selected. The selected interest region is manually aligned again as a subject.

Japanese Laid-Open Patent Application JP2001-325584A (corresponding to U.S. Pat. No. 7,035,445B) discloses an image aligning method capable of improving interpretation capacity by increasing comparison accuracy in comparing two or more images of the same subject to be compared and interpreted with each other. The image aligning method is a method of aligning two or more images. According to the image aligning method, a particular structure emphasized image obtained by emphasizing a particular structure in each of the two or more images is acquired and structural positional relationship between the acquired particular structure emphasized images is obtained. On the basis of the obtained structural positional relationship, the two or more images are aligned.

Japanese Laid-Open Patent Application JP2002-032735A (corresponding to U.S. Pat. No. 6,915,003B) discloses an image aligning method capable of achieving high accurate alignment by further suppressing misalignment of two images to be compared than conventional. The image aligning method is a method of aligning the two images of the same subject. According to the image aligning method, the two images are schematically aligned and local regions of high level of misalignment in the two images schematically aligned are selected. At least, on the selected local regions, realignment is carried out.

Japanese Laid-Open Patent Application JP2006-501922A (corresponding to WO/2004/034329) discloses a device of associating an image of the human body which should be stored with a current image with the high accuracy, desirably, in the order of millimeter or less. The image processing unit has an input for a signal of the current image of the human body volume receiving a motion with some motion phases, at least one input for a signal representing the motion phases of the human body volume included in the current image and a memory which stores previous images of the human body volume and the associated motion phases therein. The image processing unit associates the current image with the previous image having the motion phase closest to the motion phase of the current image.

Japanese Laid-Open Patent Application JP-H10-099456A (corresponding to U.S. Pat. No. 5,673,300B) discloses a method of correctly recording a treatment plan prepared for the patient in radiation treatment. The method is an operating method of a radiotherapy device for emitting at least one radiation beam having a controllable directional movement toward the patient. The method includes steps of (a) obtaining a plan tomography projecting set including a plurality of first radiography projections to the patient in predetermined treatment capacity of the patient located at a first position, (b) by activation according to a storage program using an electronic computer which receives the plan tomography projecting set, preparing a radiation treatment plan drawing at least one directional movement of the radiation beam with respect to the first position of the patient on the basis of a first plan tomography projecting set to provide desired treatment to the patient, (c) obtaining a check projecting set including a plurality of second radiography projections to the patient in predetermined treatment capacity of the patient located at a second position, (d) by activation according to the storage program using the electronic computer which receives the plan tomography projecting set and the check projecting set, comparing the plurality of second radiography projections with the corresponding projections of the first radiography projections and measured movement of the patient between the first position and the second position and (e) varying treatment for the patient according to the movement measured by using the electronic computer.

SUMMARY OF THE INVENTION

An object of the present invention is to provide a radiotherapy device control apparatus and a radiation irradiation method which can detect a predetermined area of a subject with a higher accuracy.

Another object of the present invention is to provide a radiotherapy device control apparatus and a radiation irradiation method which can adjust the predetermined area of the subject to a predetermined position of a radiotherapy device with the higher accuracy.

Another object of the present invention is to provide a radiotherapy device control apparatus and a radiation irradiation method which can improve processing speed in detecting the predetermined area of the subject with the higher accuracy.

This and other objects, features and advantages of the present invention will be readily ascertained by referring to the following description and drawings.

In order to achieve an aspect of the present invention, the present invention provides a radiotherapy device control apparatus including: a template-matching section; an affected area position calculating section; and an irradiation position control section. The radiotherapy device control apparatus controls a radiotherapy device. The radiotherapy device includes: a therapeutic radiation irradiation device which radiates therapeutic radiation, and an imager which generates an imager image of a subject by using radiation transmitted through the subject. The template matching section calculates degree of coincidence when a pattern matching is executed on the imager image with a plurality of image templates in which positional relations between an object area and a non-object area of the subject are different, and selects a specified image template having the degree of coincidence within a predetermined range from the plurality of image templates. The affected area position calculating section calculates a position of the object area by using the specified image template. The irradiation position control section judges whether a relative position of the object area with respect to the therapeutic radiation irradiation device. The irradiation position control section may move one of the therapeutic radiation irradiation device and a couch on which the subject is arranged by using a drive device provided with the radiotherapy device such that the object area is irradiated with the therapeutic radiation.

The radiotherapy device control apparatus may further includes a characteristic place extracting section which extracts a portion common to the plurality of image templates and create a characteristic place template. The affected area position calculating section calculates the position of the object area by further executing a pattern matching on the imager image with the characteristic place template.

In the radiotherapy device control apparatus, the characteristic place extracting section may create a plurality of projective templates, each of which indicates change in projection brightness obtained by projecting the plurality of image templates in one direction. The characteristic place template indicates a portion common to the plurality of projective templates.

The radiotherapy device control apparatus may further include a template creating section creates the plurality of image templates based on transmitted images imaged by using the imager.

The radiotherapy device control apparatus may further include a template creating section creates the plurality of image templates based on three-dimensional data of the subject created by a three-dimensional imaging device provided separately with the radiotherapy device.

In order to achieve another aspect of the present invention, the present invention provides a radiotherapy device control apparatus including a characteristic place extracting section; an affected area position calculating section; and an irradiation position control section. The radiotherapy device control apparatus controls a radiotherapy device. The radiotherapy device includes: a therapeutic radiation irradiation device which radiates therapeutic radiation, and an imager which generates an imager image of a subject by using radiation transmitted through the subject. The characteristic place extracting section which extracts a portion common to a plurality of transmitted images in which positional relations between an object area and a non-object area of the subject are different, and creates a characteristic place template. The affected area position calculating section calculates the position of the object area by executing a pattern matching on the imager image with the characteristic place template. The irradiation position control section judges whether a relative position of the object area with respect to the therapeutic radiation irradiation device.

The present invention provides a radiotherapy system including a radiotherapy device control apparatus according to the above-mentioned radiotherapy device control apparatus; and a radiotherapy device.

In order to achieve still another aspect of the present invention, the present invention provides a radiation irradiation method using a radiotherapy device. The radiotherapy device includes: a therapeutic radiation irradiation device which radiates therapeutic radiation, and an imager which generates an imager image of a subject by using radiation transmitted through the subject. The radiation irradiation method includes: (a) calculating degree of coincidence when a pattern matching is executed on the imager image with a plurality of image templates in which positional relations between an object area and a non-object area of the subject are different; (b) selecting a specified image template having the degree of coincidence within a predetermined range from the plurality of image templates; (c) calculating a position of the object area by using the specified image template; and (d) judging whether a relative position of the object area with respect to the therapeutic radiation irradiation device; (e) moving one of the therapeutic radiation irradiation device and a couch on which the subject is arranged by using a drive device provided with the radiotherapy device such that the object area is irradiated with the therapeutic radiation.

The radiation irradiation method may further include (g) extracting a portion common to the plurality of image templates and creating a characteristic place template, and (h) calculating the position of the object area by further executing a pattern matching on the imager image with the characteristic place template.

The radiation irradiation method may further include (i) creating a plurality of projective templates, each of which indicates change in projection brightness obtained by projecting the plurality of image templates in one direction. The characteristic place template may indicate a portion common to the plurality of projective templates.

The radiation irradiation method may further include (j) creating the plurality of image templates based on transmitted images imaged by using the imager.

The radiation irradiation method may further include (k) creating the plurality of image templates based on three-dimensional data of the subject created by a three-dimensional imaging device provided separately with the radiotherapy device.

The present invention provides a radiation irradiation method using a radiotherapy device. The radiotherapy device includes: a therapeutic radiation irradiation device which radiates therapeutic radiation, and an imager which generates an imager image of a subject by using radiation transmitted through the subject. The radiation irradiation method includes: (a) extracting a portion common to a plurality of transmitted images in which positional relations between an object area and a non-object area of the subject are different, and creating a characteristic place template; (b) calculating the position of the object area by executing a pattern matching on the imager image with the characteristic place template; and (c) judging whether a relative position of the object area with respect to the therapeutic radiation irradiation device.

In order to achieve still another aspect of the present invention, the present invention provides a computer program product with program code means for carrying out all steps according to the above-mentioned radiation irradiation method if the program runs on a computer.

The present invention provides a computer program product with program code means according to the above-mentioned radiation irradiation method which are stored on a storage means which can be read by the computer.

The radiotherapy device control apparatus and the radiation irradiation method according to the present invention can detect a predetermined area of the subject with the higher accuracy. For this reason, the radiotherapy device control apparatus and the radiation irradiation method according to the present invention can adjust the predetermined area of the subject to the predetermined position of the radiotherapy device with the higher accuracy.

DESCRIPTION OF THE PREFERRED EMBODIMENTS

The invention will be now described herein with reference to illustrative embodiments. Those skilled in the art will recognize that many alternative embodiments can be accomplished using the teachings of the present invention and that the invention is not limited to the embodiments illustrated for explanatory purposed.

Figure 1:
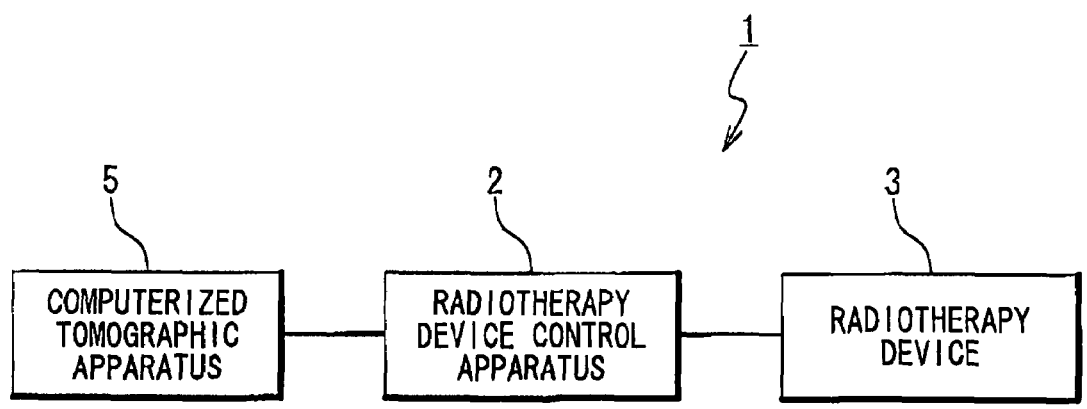
FIG. 1 is a block diagram showing a radiotherapy system of the embodiment.

An embodiment of a radiotherapy device control apparatus according to the present invention will be described below with reference to attached drawings. FIG. 1 is a block diagram showing a radiotherapy system of the embodiment. The radiotherapy device control apparatus 2, as shown in FIG. 1, is applied to the radiotherapy system 1. The radiotherapy system 1 includes the radiotherapy device control apparatus 2, a radiotherapy device 3 and a computerized tomographic apparatus (hereinafter referred to as CT) 5. The radiotherapy device control apparatus 2 is a computer exemplified by a personal computer. The radiotherapy device control apparatus 2 is connected to the radiotherapy device 3 and the CT 5 so as to be capable of transmitting information bi-directionally.

The CT 5 photographs a plurality of transmitted images by transmitting X-rays through a human body from various directions, and then subjects the plurality of transmitted images to image processing by a computer to thereby generate images of cross sections of the human body and also subjects the plurality of transmitted images to image processing by the computer to thereby generate three-dimensional data indicating inner condition of the human body. The CT 5 can be replaced with a different device, for example, an MRI device, which measures three-dimensional condition of the human body. The MRI device detects magnetism possessed by cells in the human body by using nuclear magnetic resonance and then transforms this magnetism into an image by a computer to thereby generate three-dimensional data indicating inner condition of the human body.

Figure 2:
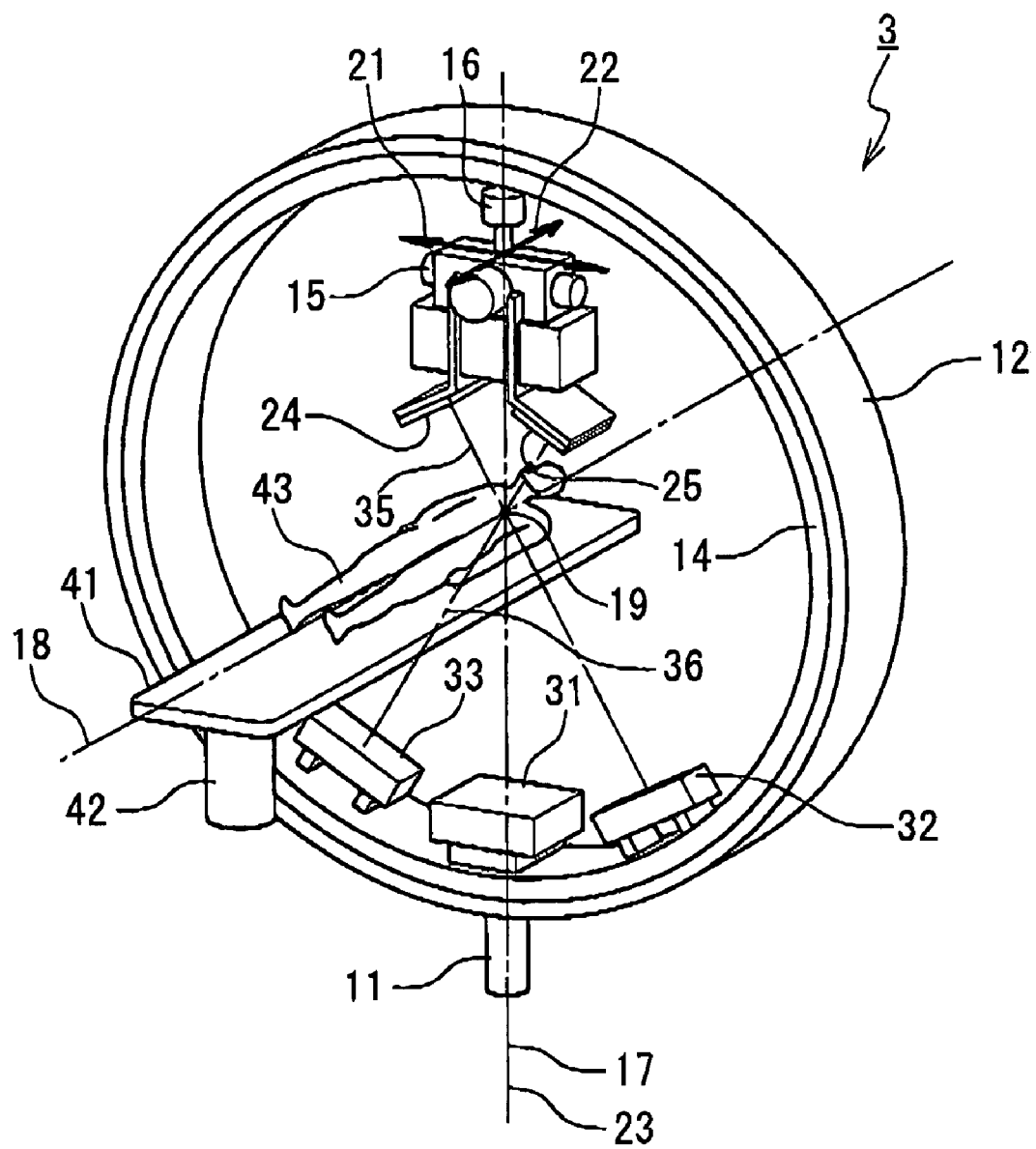
FIG. 2 is a perspective view showing a radiotherapy device of the radiotherapy system of the embodiment.

FIG. 2 is a perspective view showing the radiotherapy device 3 of the radiotherapy system 1. The radiotherapy device 3 is provided with a turning drive device 11, an O ring 12, a travel gantry 14, a head swing device 15, and a therapeutic radiation irradiation device 16. The turning drive device 11 supports the O ring 12 to a base so that the O ring 12 is rotatable around a rotation axis 17, and is controlled by the radiotherapy device control apparatus 2 to rotate the O ring 12 around the rotation axis 17. The rotation axis 17 is parallel with the vertical direction. The O ring 12 is formed into a ring shape with a rotation axis 18 serving as a center, and supports the travel gantry 14 so that the travel gantry 14 is rotatable around the rotation axis 18. The rotation axis 18 is perpendicular to the vertical direction, and passes through an isocenter 19 included in the rotation axis 17. The rotation axis 18 is further fixed with respect to the O ring 12, that is, rotates around the rotation axis 17 together with the O ring 12. The travel gantry 14 is formed into a ring shape with around the rotation axis 18 serving as a center, and so arranged as to be concentric with the ring of the O ring 12. The radiotherapy device 3 further provided with a traveling drive device (not shown). The traveling drive device is controlled by the radiotherapy device control apparatus 2 to rotate the travel gantry 14 around the rotation axis 18.

The therapeutic radiation irradiation device 16 is disposed on the inner side of the travel gantry 14. The therapeutic radiation irradiation device 16 is controlled by the radiotherapy device control apparatus 2, thereby radiating a therapeutic radiation 23.

The head swing device 15 is fixed inside the ring of the travel gantry 14 to support the therapeutic radiation irradiation device 16 to the travel gantry 14. The head swing device 15 has a pan axis 21 and a tilt axis 22. The pan axis 21 is fixed with respect to the travel gantry 14 and is parallel to the rotation axis 18 without intersecting therewith. The tilt axis 22 is fixed with respect to the travel gantry 14 and orthogonal to the pan axis 21. The head swing device 15 is controlled by the radiotherapy device control apparatus 2 to rotate the therapeutic radiation irradiation device 16 around the pan axis 21 and also rotates the therapeutic radiation irradiation device 16 around the tilt axis 22.

Once the therapeutic radiation irradiation device 16 is supported by the travel gantry 14 as described above and is adjusted by the head swing device 15 so as to be directed toward the isocenter 19, the therapeutic radiation 23 always passes approximately through the isocenter 19 even when the O ring 12 is rotated by the turning drive device 11 or when the travel gantry 14 is rotated by the traveling drive device. That is, the therapeutic radiation 23 can be irradiated toward the isocenter 19 from any direction through traveling and rotation.

Since the therapeutic radiation irradiation device 16 is a heavy object, the O ring itself may be mechanically deformed due to traveling and rotation. Furthermore, there may be a case that affected area does not correspond to the isocenter. In such case, following setting of traveling and rotation, the head swing device 15 can readjust so that the therapeutic radiation irradiation device 16 may face the isocenter 19 or the affected area.

The radiotherapy device 3 is further provided with a plurality of imager systems. Specifically, the radiotherapy device 3 is provided with diagnostic X-ray sources 24 and 25, and sensor arrays 32 and 33. The diagnostic X-ray source 24 is supported by the travel gantry 14. The diagnostic X-ray source 24 is arranged inside the ring of the travel gantry 14 and at position such that a line segment linking from the isocenter 19 to the diagnostic X-ray source 24 and a line segment linking from the isocenter 19 to the therapeutic radiation irradiation device 16 forms an acute angle. The diagnostic X-ray source 24 is controlled by the radiotherapy device control apparatus 2 to irradiate diagnostic X-rays 35 toward the isocenter 19. The diagnostic X-rays 35 are radiated from one point included in the diagnostic X-ray source 24, and are cone beams of a conical shape with the aforementioned point serving as a vertex. The diagnostic X-ray source 25 is supported by the travel gantry 14. The diagnostic X-ray source 25 is arranged inside the ring of the travel gantry 14 and at position such that a line segment linking from the isocenter 19 to the diagnostic X-ray source 25 and a line segment linking from the isocenter 19 to the therapeutic radiation irradiation device 16 forms an acute angle. The diagnostic X-ray source 25 is controlled by the radiotherapy device control apparatus 2 to irradiate diagnostic X-rays 36 toward the isocenter 19. The diagnostic X-rays 36 are radiated from one point included in the diagnostic X-ray source 25, and are cone beams of a conical shape with the aforementioned point serving as a vertex.

The sensor array 32 is supported by the travel gantry 14. The sensor array 32 receives the diagnostic X-ray 35 radiated by the diagnostic X-ray source 24 and transmitted through a photographic subject on the periphery of the isocenter 19 to generate a transmitted image of the photographic subject. The sensor array 33 is supported by the travel gantry 14. The sensor array 33 receives the diagnostic X-ray 36 radiated by the diagnostic X-ray source 25 and transmitted through the photographic subject on the periphery of the isocenter 19 to generate a transmitted image of the photographic subject. The sensor arrays 32 and 33 are exemplified by FPDs (Flat Panel Detectors) and X-rays II (Image Intensifiers).

According to such imager system, the transmitted images using the isocenter 19 as the center are generated on the basis of image signals from the sensor arrays 32, 33.

The diagnostic X-ray source 24 can also be arranged at a position such that a line segment linking from the isocenter 19 to the diagnostic X-ray source 24 and a line segment linking from the isocenter 19 to the therapeutic radiation irradiation device 16 forms an obtuse angle. That is, the sensor array 32 is arranged at position such that a line segment linking from the isocenter 19 to the sensor array 32 and a line segment linking from the isocenter 19 to the therapeutic radiation irradiation device 16 forms an acute angle. The diagnostic X-ray source 25 can also be arranged at position such that a line segment linking from the isocenter 19 to the diagnostic X-ray source 25 and a line segment linking from the isocenter 19 to the therapeutic radiation irradiation device 16 forms an obtuse angle. That is, the sensor array 33 is arranged at position such that a line segment linking from the isocenter 19 to the sensor array 33 and a line segment linking from the isocenter 19 to the therapeutic radiation irradiation device 16 forms an acute angle. In this case, the sensor arrays 32 and 33 are less likely to be irradiated with the therapeutic radiation 23 radiated from the therapeutic radiation irradiation device 16, which is preferable.

The radiotherapy device 3 is further provided with a sensor array 31. The sensor array 31 is arranged so that a line segment linking from the sensor array 31 to the therapeutic radiation irradiation device 16 passes the isocenter 19 and is fixed on the inner side of the travel gantry 14. The sensor array 31 receives the therapeutic radiation 23 radiated by the therapeutic radiation irradiation device 16 and transmitted through a subject around the isocenter 19 to generate a transmitted image of the subject. The sensor array 31 is exemplified by an FPD (Flat Panel Detector) and X-rays II (Image Intensifier).

The radiotherapy device 3 is further provided with a couch 41 and a couch drive device 42. The couch 41 is used for laying a patient 43 to be treated by the radiotherapy system 1. The couch 41 is provided with a fixing tool (not shown). This fixing tool fixes the patient to the couch 41 so that he or she does not move. The couch drive device 42 supports the couch 41 to the base and is controlled by the radiotherapy device control apparatus 2 to move the couch 41.

Figure 3:
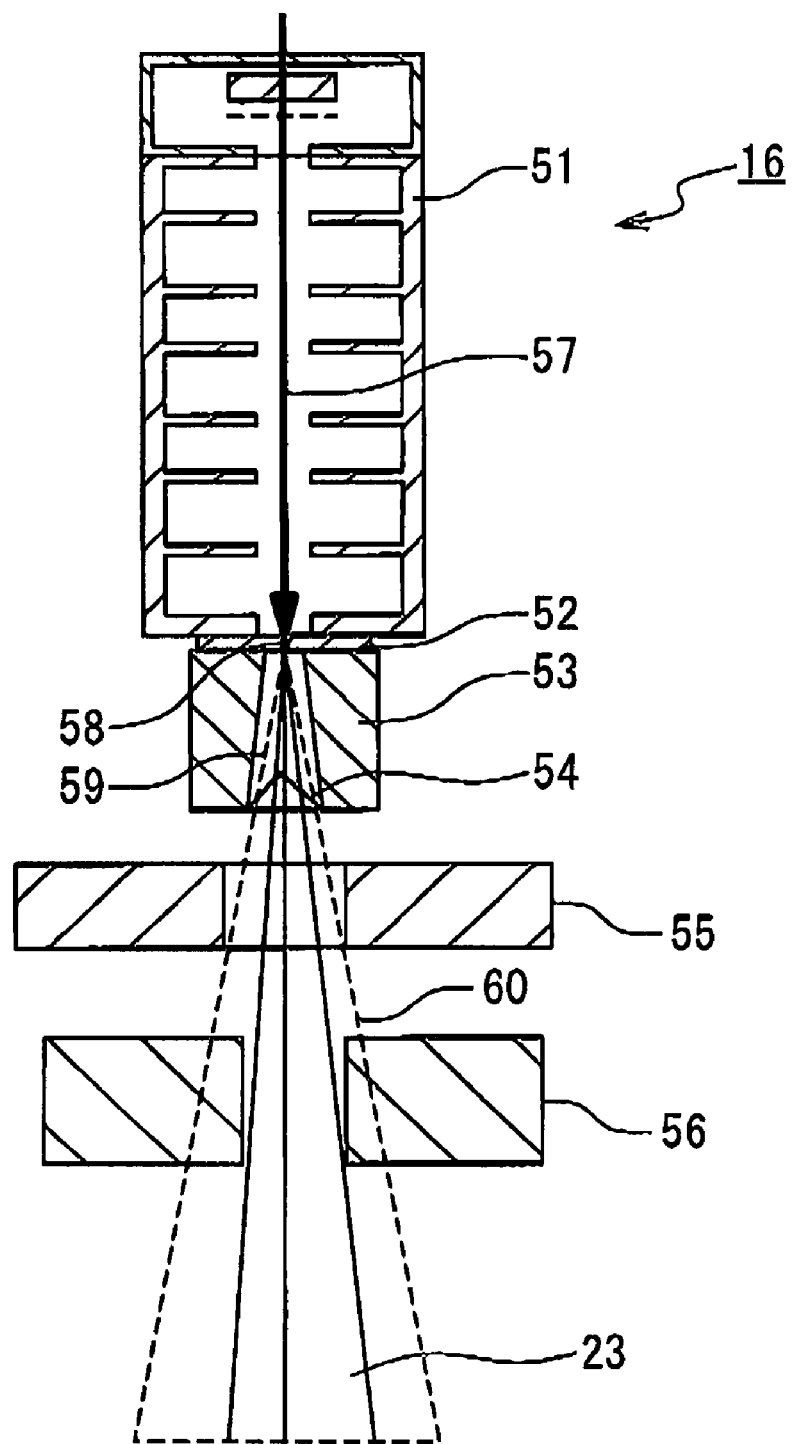
FIG. 3 is a sectional view showing an example of the therapeutic radiation irradiation device of the radiotherapy system of the embodiment.

FIG. 3 is a sectional view showing an example of the therapeutic radiation irradiation device 16 of the radiotherapy system 1. The therapeutic radiation irradiation device 16 is provided with an electron beam accelerator 51, an X-ray target 52, a primary collimator 53, a flattening filter 54, a secondary collimator 55 and a multileaf collimator 56. The electron beam accelerator 51 radiates an electron beam 57 generated by accelerating electrons onto the X-ray target 52. The X-ray target 52 is made of a material containing elements having relatively high atomic number. Tungsten, tungsten alloy and the like may be used as the material. The X-ray target 52 radiates a radiation 59 generated by bremsstrahlung (braking radiation) when the electron beam 57 is irradiated. The radiation 59 is radiated substantially along a straight line passing a virtual point radiation source 58 as a point included in the X-ray target 52. The primary collimator 53 is made of a material containing elements having relatively high atomic number. Lead, tungsten and the like may be used as the material. The primary collimator 53 shields the radiation 59 so that the radiation 59 may be irradiated onto only a desired region. The flattening filter 54 is made of aluminum or the like and shaped like a plate on which a substantially conical protrusion is formed. The protrusion is disposed on the side of the X-ray target 52 of the flattening filter 54. The flattening filter 54 generates a radiation 60 whose dose in a predetermined region on a plane perpendicular to the radiating direction is distributed substantially uniformly by properly attenuating the dose of passing radiation 59. That is, the flattening filter 54 is formed so that the radiation 60 may have uniform intensity distribution. The secondary collimator 55 is made of a material containing elements having relatively high atomic number. Lead, tungsten and the like may be used as the material. The secondary collimator 55 shields the radiation 60 so that the radiation 60 may be irradiated onto only a desired region. The radiation 60 is partially shielded by the multileaf collimator 56 controlled by the radiotherapy device control apparatus 2 to generate the therapeutic radiation 23 based on a separately created treatment plan. The multileaf collimator 56 is controlled by the radiotherapy device control apparatus 2, thereby partially shielding the radiation 60 to generate the therapeutic radiation 23. That is, the multileaf collimator 56 is controlled by the radiotherapy device control apparatus 2, thereby partially shielding the radiation 60 to control shape of irradiation field at the time when the therapeutic radiation 23 is irradiated to the patient.

Figure 4:
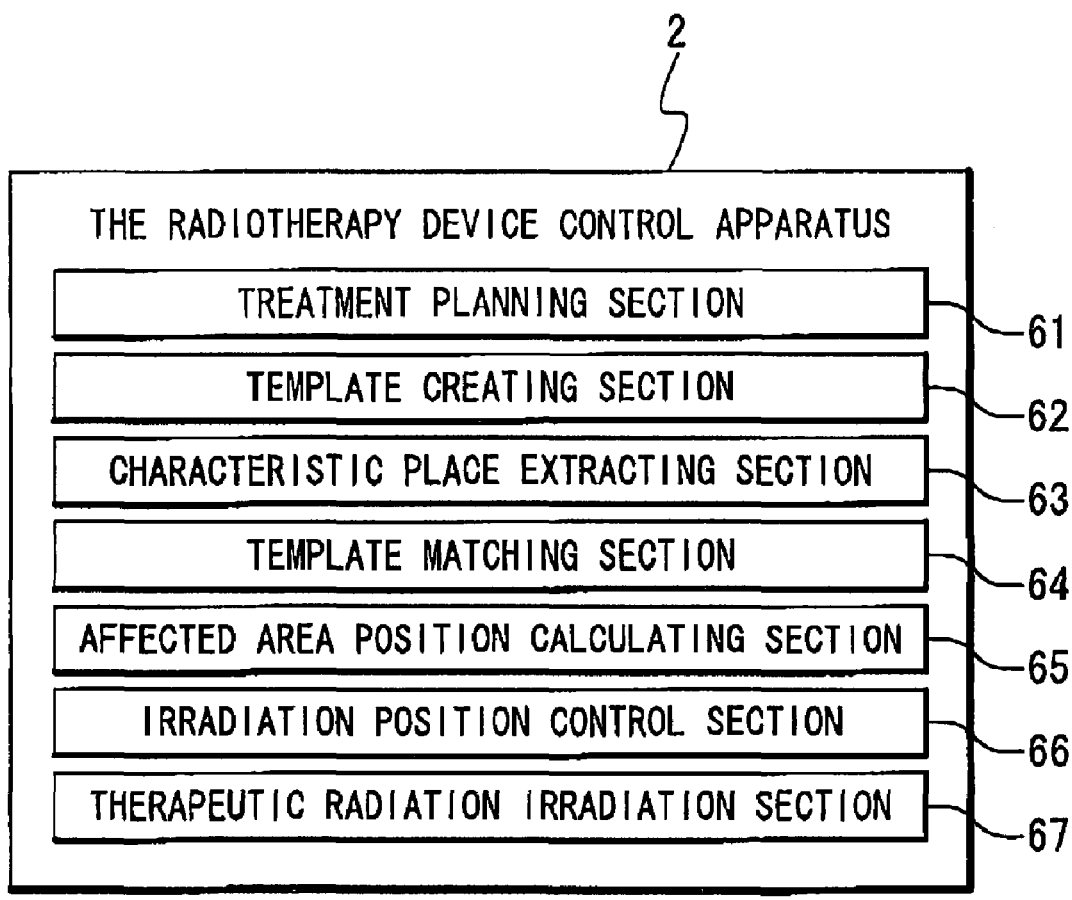
FIG. 4 is a block diagram of a radiotherapy device control apparatus of the radiotherapy system of the embodiment.

FIG. 4 is a block diagram showing the radiotherapy device control apparatus 2 of the radiotherapy system 1. The radiotherapy device control apparatus 2 is a computer, and is provided with a CPU, a storage device, an input device, an output device, and an interface (all not shown). The CPU executes a computer program installed in the radiotherapy device control apparatus 2 to control the storage device, the input device, the output device and the interface thereof. The storage device stores the computer program, information used by the CPU, and information generated by the CPU. The input device supplies to the CPU information generated through user's operation. The input device is exemplified by a keyboard and a mouse. The output device outputs information generated by the CPU in a manner such that the information can be recognized by the user. The output device is exemplified by a display. The interface outputs to the CPU information generated by an external device connected to the radiotherapy device control apparatus 2 and outputs to the external device information generated by the CPU. The external device includes the CT 5 and the radiotherapy device 3.

The radiotherapy device control apparatus 2 includes a treatment planning section 61, a template creating section 62, a characteristic place extracting section 63, a template matching section 64, an affected area position calculating section 65, an irradiation position control section 66 and a therapeutic radiation irradiation section 67, as the computer program.

The treatment planning section 61 collects from the CT 5 three-dimensional data generated by the CT 5 and indicating positional relationship between an affected area of the patient 43 and the organs around the affected area. On the basis of the three-dimensional data and information supplied by the user, the treatment planning section 61 creates a treatment plan. The treatment plan indicates irradiation angles at which the affected area of the patient 43 is irradiated with the therapeutic radiation 23 and the dosage and property of the therapeutic radiation 23 irradiated from each of the irradiation angles. The treatment plan further indicates imaging angles at which the diagnostic X-rays 35 and 36 are irradiated such that transmitted images imaged by transmission of the diagnostic X-rays 35 and 36 through the patient 43 displays the affected area of the patient 43 more precisely when the therapeutic radiation 23 is irradiated from various irradiation angles.

The template creating section 62 irradiates the diagnostic X-ray 35 by using the diagnostic X-ray source 24 and images a plurality of transmitted images of the patient 43 which are generated by using the sensor array 32 on the basis of the diagnostic X-ray 35. The plurality of transmitted images is imaged when positional relationship between the affected area of the patient 43 and a bone of the patient 43 is varied. In such case, it may be difficult to execute complete identification of character of the affected area using only the transmitted images. The bone may be replaced with another object clearly seen on the transmitted images. An organ different from the affected area and a gold marker embedded in a region moving together with the affected area of the patient 43 may be used as the object. Similarly, the template creating section 62 irradiates the diagnostic X-ray 36 by using the diagnostic X-ray source 25 and images a plurality of transmitted images of the patient 43 which is generated by using the sensor array 33 on the basis of the diagnostic X-ray 36. Similarly, the template creating section 62 radiates the therapeutic radiation 23 by using the therapeutic radiation irradiation device 16 and images a plurality of transmitted images of the patient 43 which is generated by using the sensor array 31 on the basis of the therapeutic radiation 23.

Furthermore, the template creating section 62 displays the transmitted images on the display and sets regions of the transmitted images where the affected area of the patient 43 is shown on the basis of the information input by the user. This setting is carried out, for example, by enclosing the region with a rectangular frame. The following description is premised on the assumption that each region is set by being enclosed with the frame. Each frame is disposed so that the positional relation between the frame and the region where the affected area is shown may coincide among the plurality of transmitted images. The template creating section 62 extracts the regions enclosed with the frames from the plurality of transmitted images and creates a plurality of image templates. The template creating section 62 creates a projective template for each image template.

The characteristic place extracting section 63 creates characteristic place templates on the basis of the plurality of projective templates prepared by the template creating section 62. The characteristic place template indicates a characteristic common to another projective template among characteristics of the projective template and a region where the common characteristic appears.

The template matching section 64 irradiates the diagnostic X-ray 35 by using the diagnostic X-ray source 24 and images the transmitted images of the patient 43 which are generated by using the sensor array 32 on the basis of the diagnostic X-ray 35. The template matching section 64 extracts the region which resembles the plurality of image templates prepared by the template creating section 62 most from the transmitted images and calculates position and degree of coincidence by using a pattern-matching image processing method. The degree of coincidence indicates how the region resembles the image template, and as the degree of coincidence is larger, the region resembles the image template more. An optical flow method and a high-speed template matching method using monotonic function of normalized correlation operation may be used as the pattern-matching image processing method. A gradient method and a block matching method may be used as the optical flow method. The template matching section 64 selects an image template having the degree of coincidence larger than a predetermined value among the plurality of image templates prepared by the template creating section 62. The predetermined value may be set in advance. A matching percentage (degree of coincidence) of 60% may be used as the set value. This value can be corrected or input by the user separately.

Similarly, the template matching section 64 radiates the diagnostic X-ray 36 by using the diagnostic X-ray source 25 and images the transmitted images of the patient 43 which are generated by using the sensor array 33 on the basis of the diagnostic X-ray 36. The template matching section 64 extracts the region which resembles the plurality of image templates prepared by the template creating section 62 most from the transmitted images and calculates position and degree of coincidence by using a pattern-matching image processing method. The template matching section 64 selects an image template having the degree of coincidence larger than a predetermined value among the plurality of image templates prepared by the template creating section 62. The predetermined value may be set in advance. A matching percentage of 60% may be used as the set value. This value can be corrected or input by the user separately.

Similarly, the template matching section 64 irradiates the diagnostic X-ray 23 by using the therapeutic radiation irradiation device 16 and images the transmitted images of the patient 43 which are generated by using the sensor array 31 on the basis of the therapeutic radiation 23. The template matching section 64 extracts the region which resembles the plurality of image templates prepared by the template creating section 62 most from the transmitted images and calculates position and degree of coincidence by using a pattern matching image processing method. The template matching section 64 selects an image template having the degree of coincidence larger than a predetermined value among the plurality of image templates prepared by the template creating section 62. The predetermined value may be set in advance. A matching percentage of 60% may be used as the set value. This value can be corrected or input by the user separately.

The affected area position calculating section 65 calculates position of the affected area on the basis of the image template selected by the template matching section 64 and the characteristic place templates prepared by the characteristic place extracting section 63.

The irradiation position control section 66 moves the therapeutic radiation irradiation device 16 by using the head swing device 15 so that the therapeutic radiation 23 is transmitted through a position calculated by the affected area position calculating section 65. The irradiation position control section 66 can also move the therapeutic radiation irradiation device 16 by further using the turning drive device 11 or the traveling drive device for rotating the travel gantry 14 around the rotation axis 18, or can move the couch 41 by further using the couch drive device 42, so that the therapeutic radiation 23 is transmitted through the position. In this case, the irradiation position control section 66 uses the turning drive device 11 or the traveling drive device for rotating the travel gantry 14 around the rotation axis 18 or the head swing device 15 preferentially prior to the couch drive device 42. Such movement reduces the load of moving the patient 43 and does not cause a change of the character of the moving affected area, which is preferable.

The therapeutic radiation irradiation section 67, after the therapeutic radiation irradiation device 16 and so on is moved by the irradiation position control section 66, irradiates the affected area with the therapeutic radiation 23 having the dose indicated in the treatment plan by using the therapeutic radiation irradiation device 16.

Figure 5:
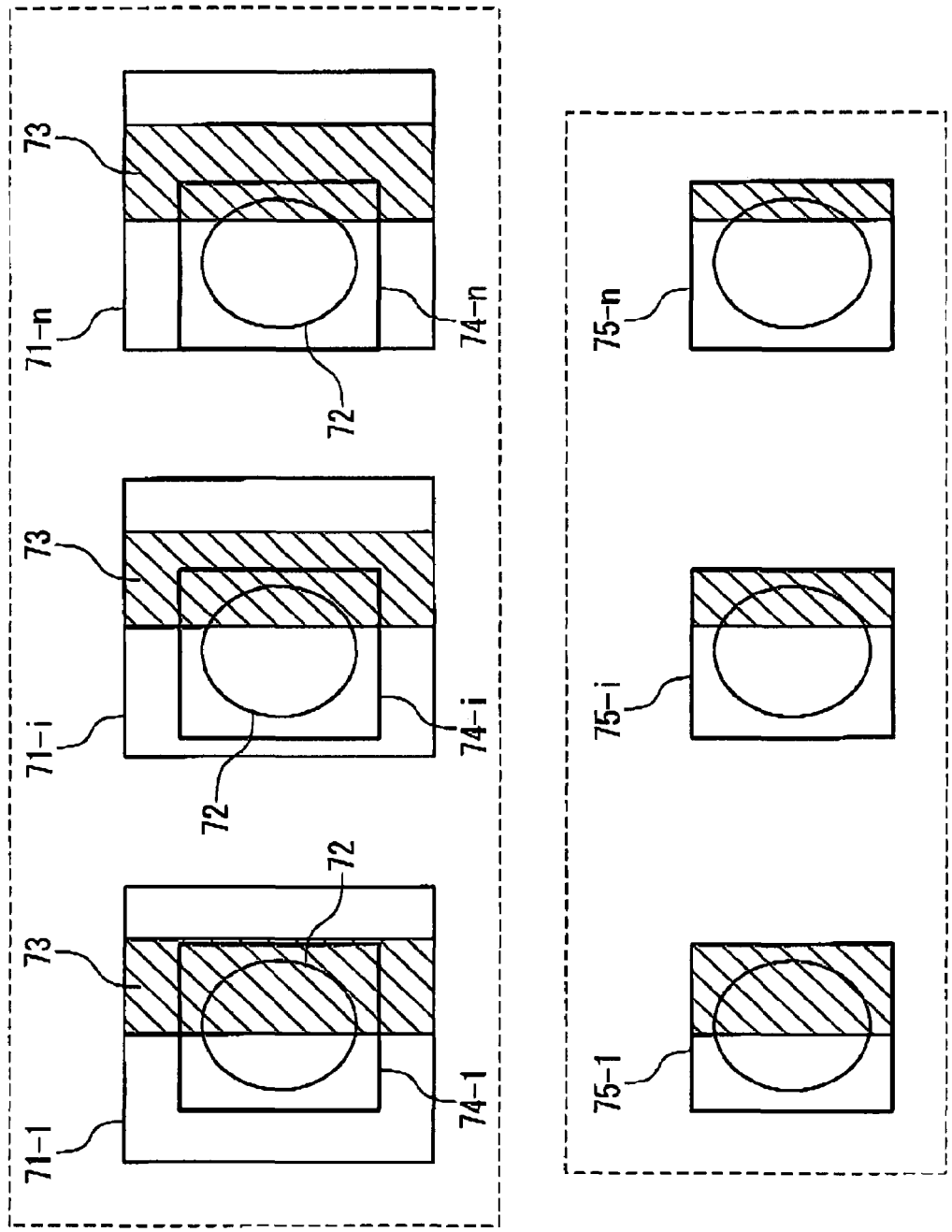
FIG. 5 is a view showing examples of transmitted images and image templates of the embodiment.

FIG. 5 is a view showing examples of a plurality of images imaged by the template creating section 62. The plurality of transmitted images 71-1 to 71-n (n=2, 3, 4, . . . ) are imaged from the same direction at different times. That is, the images are imaged by using one of the diagnostic X-ray 35, the diagnostic X-ray 36 and the therapeutic radiation 23. An affected area 72 and a bone 73 of the patient 43 are shown in each of the transmitted images 71-i (i=1, 2, 3, . . . , n). Positions of the affected area 72 and the bone 73 which are shown in the plurality of transmitted images 71-1 to 71-n vary depending on the transmitted images 71-1 to 71-n. That is, the plurality of transmitted images 71-1 to 71-n is imaged at times when positional relationship between the affected area 72 and the bone 73 varies, for example, phase of breath varies. Brightness of a pixel located at a position (x,y) of the transmitted image 71-i is defined by using a width $S_{ix}$ of the transmitted image 71-i and a height $S_{iy}$ of the transmitted image 71-i according to the following formula:

$I_i(x,y)(0 \leq x \leq S_{ix}, 0 \leq y \leq S_{iy})$

At this time, the template creating section 62 displays the plurality of transmitted images 71-1 to 71-n on the display one by one. Looking at the transmitted image 71-i displayed on the display, the user places a frame 74-i enclosing the affected area 72 in the transmitted image 71-i by using the input device. The template creating section 62 extracts each of the regions enclosed with the frames 74-1 to 74-n from the plurality of transmitted images 71-1 to 71-n and creates a plurality of image templates 75-1 to 75-n.

Figure 6:
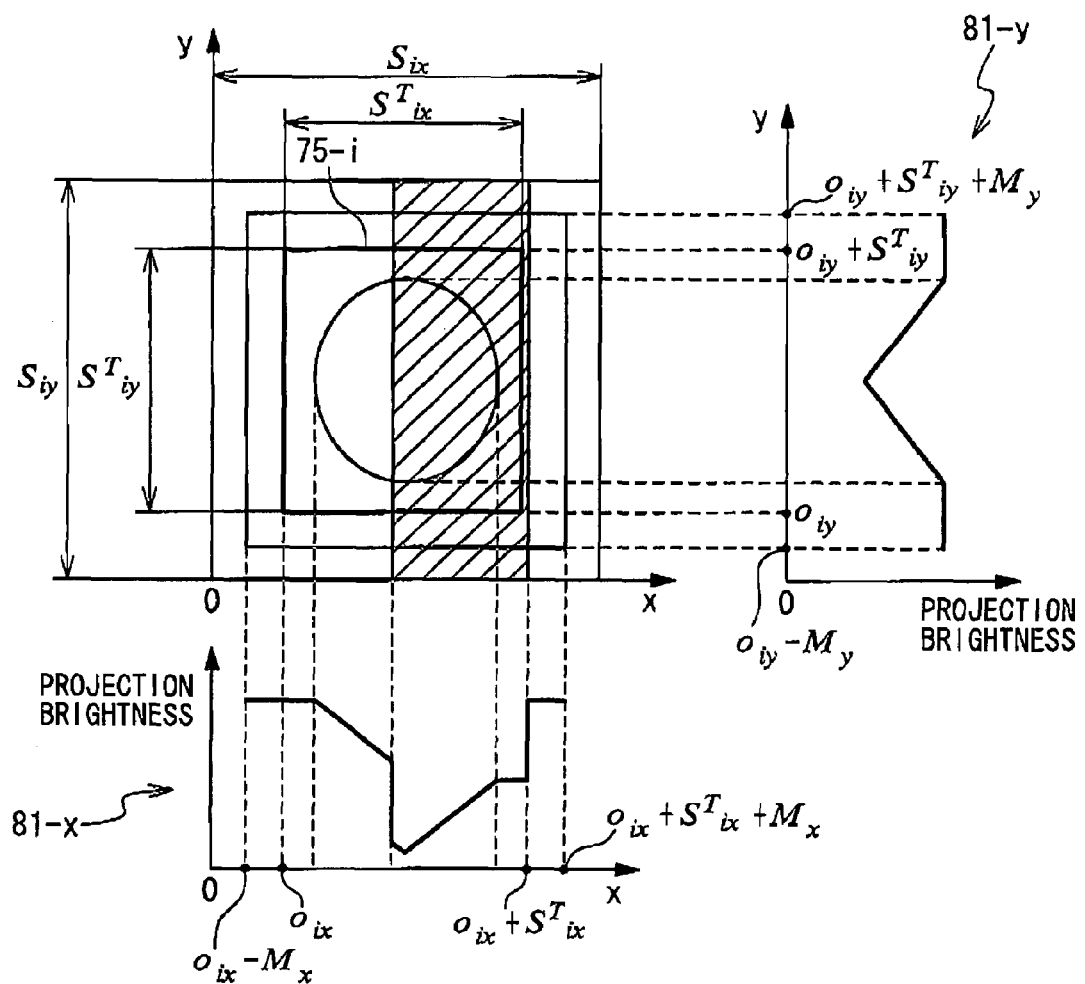
FIG. 6 is a view showing examples of an image template and a projective template of the embodiment.

FIG. 6 is a view showing examples of the projective template created by the template creating section 62. The projective template is created based on the image template 75-i and is formed of a height direction projective template 81-x and a width direction projective templates 81-y. The height direction projective template 81-x shows change in projection brightness obtained by projecting brightness on the periphery of the image template 75-i in the transmitted image 71-i in the height direction. The projection brightness $T^x_i(x)$ is expressed by using a position $o_{ix}$ of the left end of the image template 75-i in the transmitted image 71-i in the width direction, a width $S^T_{ix}$ of the image template 75-i, a height $S^T_{iy}$ and a constant Mx according to the following formula.

[Formula 1]

$$T^x_i(x) = \sum_{o_{iy} \leq y < o_{iy}+S^T_{iy}} I_i(x, y)/S^T_{iy} \cdot (o_{ix} - M_x \leq x < o_{ix} + S^T_{ix} + M_x) \quad (1)$$

Here, the constant $M_x$ depends on size of a surrounding area of the relevant template. In consideration of the case where an affected area characteristic lies in the boundary region of the frame enclosing the affected area 72, the constant is set when a projection range for extracting the affected area characteristic is set to be larger than the frame 74-i enclosing the affected area 72. The width direction projective templates 81-y shows change in projection brightness obtained by projecting brightness on the periphery of the image template 75-i in the transmitted image 71-i in the width direction. The projection brightness $T^y_i(y)$ is expressed by using a position $O_{iy}$ of the lower end of the image template 75-i in the transmitted image 71-i in the height direction, the width $S^T_{ix}$ of the image template 75-i, the height $S^T_{iy}$ and a constant $M_y$ according to the following formula.

[Formula 2]

$$T^y_i(y) = \sum_{o_{ix} \leq x < o_{ix}+S^T_{ix}} I_i(x, y)/S^T_{ix} \cdot (o_{iy} - M_y \leq y < o_{iy} + S^T_{iy} + M_y) \quad (2)$$

Here, the constant $M_y$ depends on size of a surrounding area of the relevant template. In consideration of the case where an affected area characteristic lies in the boundary region of the frame enclosing the affected area 72, the constant is set when a projection range for extracting the affected area characteristic is set to be larger than the frame 74-i enclosing the affected area 72.

The characteristic place extracting section 63 calculates a plurality of width direction characteristic place templates on the basis of the plurality of height direction projective templates calculated based on the plurality of transmitted images imaged at the same position, and calculates a plurality of height direction characteristic place templates on the basis of the plurality of width direction projective templates calculated based on the plurality of transmitted images imaged at the same position.

Figure 7:
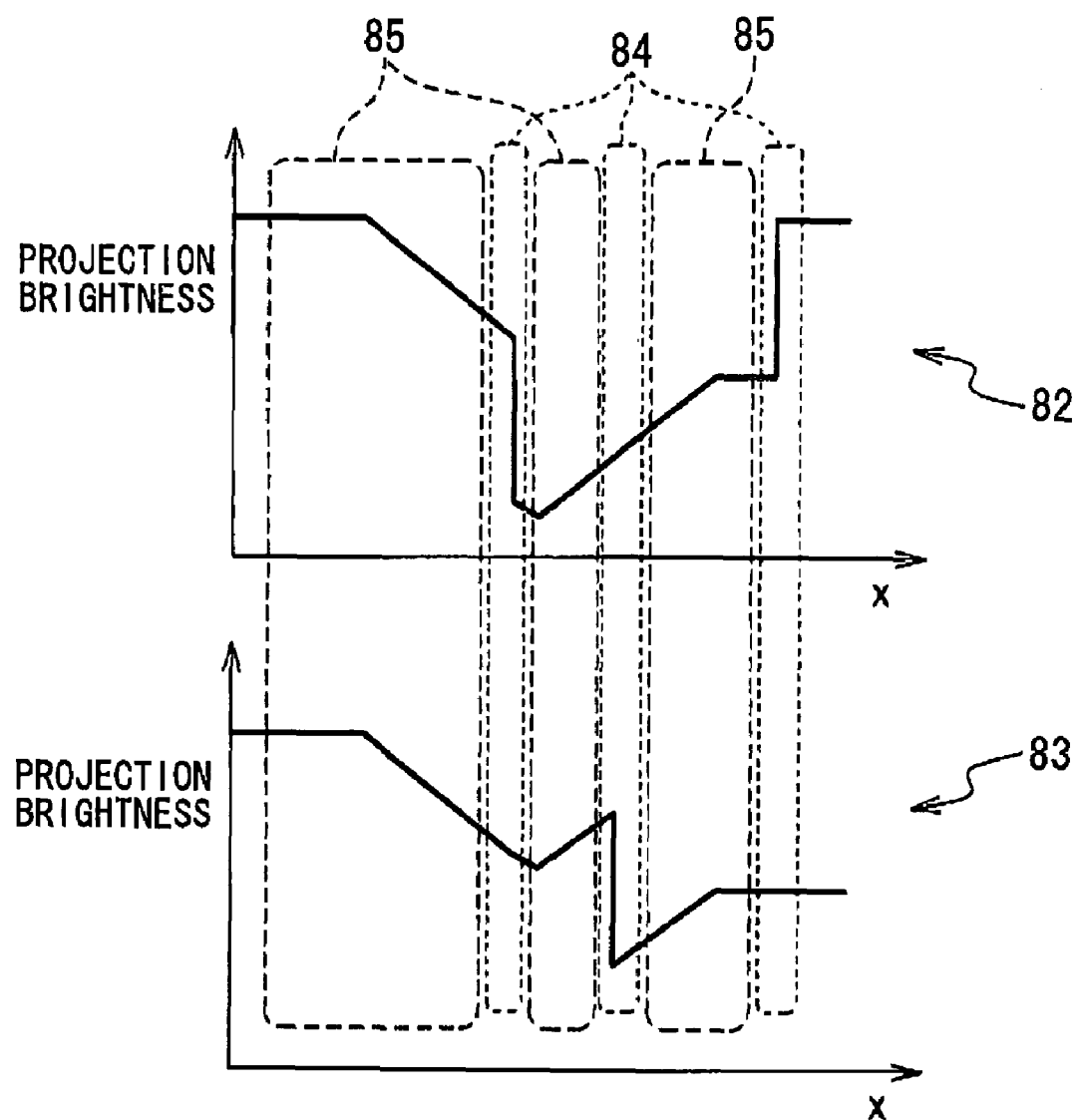
FIG. 7 is a graph showing examples of characteristic place templates of the embodiment.

FIG. 7 is a view showing width direction characteristic place templates calculated by the characteristic place extracting section 63. The width direction characteristic place templates 85 are formed of a part of the height direction projective template 82 calculated based on the transmitted image 71-i. Comparing the height direction projective templates 82 with a plurality of height direction projective templates 83 calculated based on the other plurality of transmitted images imaged from the same direction as the transmitted image 71-i, the part shows variation in projection brightness in sections where the tendency of variation in projection brightness is the same in a domain of a position x. The variation in projection brightness indicates increase and decrease of projection brightness with respect to the position x irrespective of an absolute value of projection brightness. For example, the variation is expressed by showing variation of the value obtained by differentiating projection brightness of the height direction projective template 82 with respect to the position x.

Width direction non-characteristic place templates 84 show variation in projection brightness in sections where the tendency of variation in projection brightness is varied in the domain of the position x, and indicates no image element of the affected area 72.

As in the case of the width direction characteristic place templates, height direction characteristic place templates are calculated by the characteristic place extracting section 63. That is, the height direction characteristic place templates are formed of a part of the width direction projective template calculated based on the transmitted image 71-*i*. Comparing the width direction projective templates with a plurality of width direction projective templates calculated based on the other plurality of transmitted images imaged from the same direction as the transmitted image 71-*i*, the part shows variation in projection brightness in sections where the tendency of variation in projection brightness is the same in a domain of a position y.

At this time, the affected area position calculating section 65 calculates position in the width direction of a region which resembles the width direction characteristic place template most and position in the height direction of a region which resembles the height direction characteristic place template most from regions extracted by template matching of the transmitted images imaged by the template matching section 64. The affected area position calculating section 65 calculates position of the affected area on the basis of the position in the width direction and the position in the height direction.

Such width direction characteristic place templates and the height direction characteristic place templates have less amount of information than a two-dimensional image. For this reason, the radiotherapy device control apparatus 2 can reduce loads applied to the CPU and make processing speed higher by performing template matching using the width direction characteristic place templates and the height direction characteristic place templates. However, if processing can be made faster according to the other techniques, it is possible to extract common characteristic and execute processing using a two-dimensional image, not the width direction projective templates. Well-known methods such as Hough transform and a peripheral extraction method using dynamic peripheral model may be applied to the processing in this case.

Figure 8:
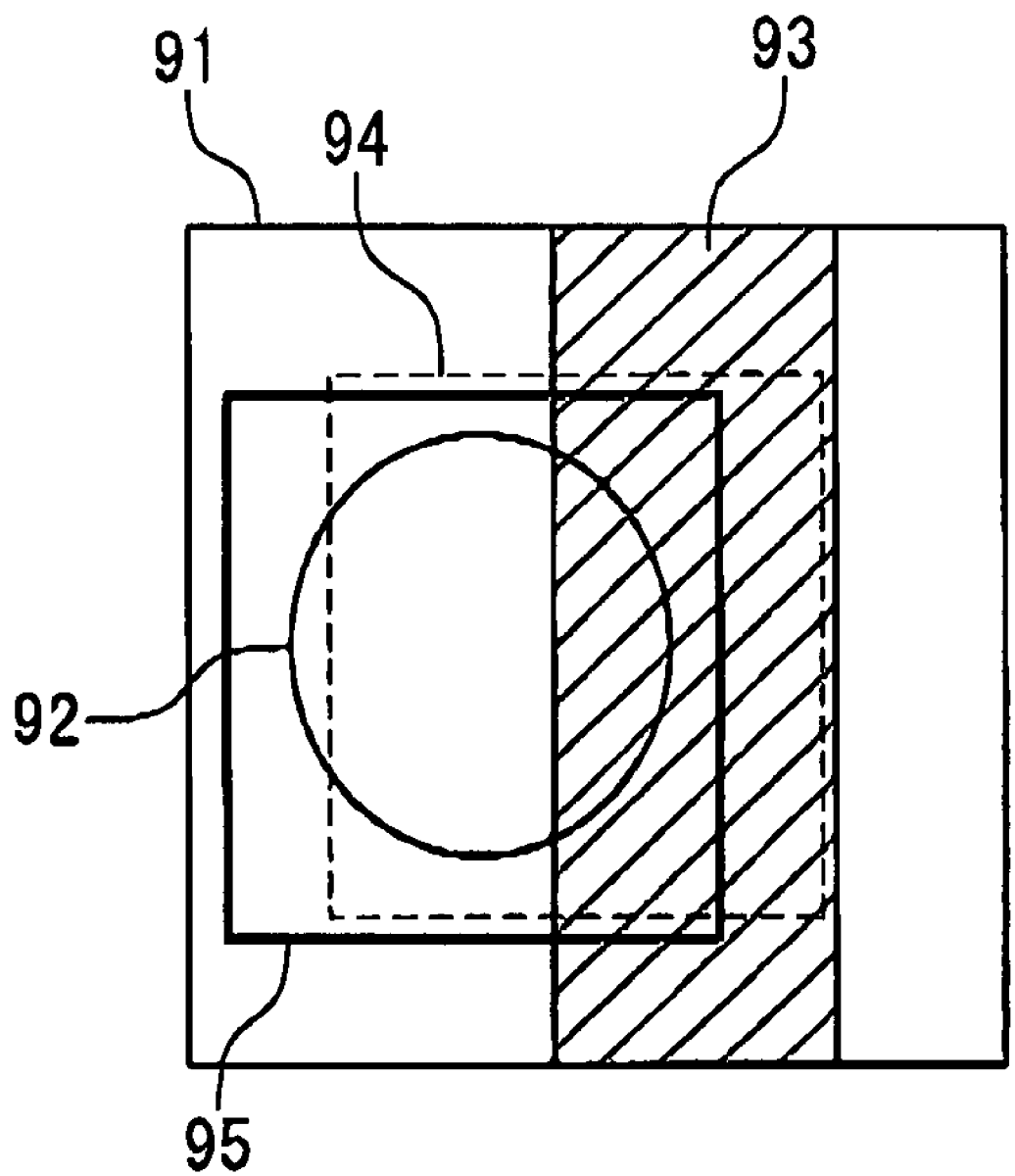
FIG. 8 is a view showing examples of transmitted images and image templates of the embodiment.

FIG. 8 is a view showing the transmitted image imaged by the template matching section 64 and position calculated by the template matching section 64. An affected area 92 and a bone 93 of the patient 43 are shown in a transmitted image 91. Since the bone 93 has higher density than the affected area 92, the bone 93 is shown densely than the affected area 92 in the transmitted image 91. At this time, there are cases where position of the region which resembles a certain image template most is influenced by the region where the bone 93 is shown and thus, does not correspond to the region where the affected area 92 is shown. For example, the position calculated by the image template 94 may be different from the position calculated by another image template 95. At this time, it is assumed that the image template with high degree of coincidence among the plurality of image templates which are different from one another in positional relationship between the affected area 92 and the bone 93 imaged by the template matching section 64 corresponds to a position of the region where the affected area 92 is shown with the higher accuracy.

The embodiment of the radiation irradiation method according to the present invention is carried out by the radiotherapy system 1, and includes an operation of creating a treatment plan, a template preparing operation and a treatment operation.

In the operation of creating a treatment plan, the user first gathers three-dimensional data of an affected area of the patient 43 and a portion around the affected area by using the CT 5. The radiotherapy device control apparatus 2, based on the three-dimensional data generated by the CT 5, generates an image indicating the affected area of the patient 43 and organs at the periphery of the affected area. The user looks the image by using the radiotherapy device control apparatus 2, and identifies the position of the affected area. The user, based on the image, further creates a treatment plan by using the treatment planning section 61, and inputs the treatment plan to the radiotherapy device control apparatus 2. The treatment plan indicates irradiation angles at which the affected area of the patient 43 is irradiated with the therapeutic radiation 23, and the dosage and property of the therapeutic radiation 23 irradiated at each of the irradiation angles. The treatment plan further indicates imaging angles at which the diagnostic X-rays 35 and 36 are irradiated when the therapeutic radiation 23 is irradiated at various irradiation angles.

The template creating operation is performed immediately before the treatment operation. First, the user fixes the patient 43 on the couch 41 of the radiotherapy device 3 at the same position as the position when the three-dimensional data is collected by the CT 5. The radiotherapy device control apparatus 2 aligns the therapeutic radiation irradiation device 16, the diagnostic X-ray sources 24, 25 and the patient 43 by using the turning drive device 11, the traveling drive device and the couch drive device 42 so that therapeutic radiation 23 may be irradiated to the patient 43 at the irradiation angles shown in the treatment plan and that the diagnostic X-rays 35, 36 may be irradiated to the patient 43 at the imaging angles shown in the treatment plan.

The radiotherapy device control apparatus 2 irradiates the diagnostic X-rays 35 to the patient 43 by using the diagnostic X-ray source 24 and images the plurality of transmitted images which are different from one another in positional relationship between the affected area of the patient 43 and the bone of the patient 43 by using the sensor array 32. Furthermore, the radiotherapy device control apparatus 2 irradiates the diagnostic X-ray 36 to the patient 43 by using the diagnostic X-ray source 25 and images the plurality of transmitted images which are different from one another in positional relationship between the affected area of the patient 43 and the bone of the patient 43 by using the sensor array 33.

The radiotherapy device control apparatus 2 displays the transmitted images on the display one by one. Looking at the transmitted image displayed on the display, the user places the frame enclosing the affected area of the patient 43 in the transmitted image by using the input device. The radiotherapy device control apparatus 2 extracts the region enclosed with the frame from the transmitted image to create the image template. The radiotherapy device control apparatus 2 repeats such operation for each of the imaged transmitted images to create the plurality of image templates.

The radiotherapy device control apparatus 2 creates the projective template for each image template. Furthermore, the radiotherapy device control apparatus 2 calculates one width direction characteristic place template and one height direction characteristic place template on the basis of the plurality of image templates prepared based on the plurality of transmitted images imaged at the same position.

The treatment operation has a tracking operation and an irradiating operation. The tracking operation and the irradiating operation are repeatedly performed one after the other.

Figure 9:
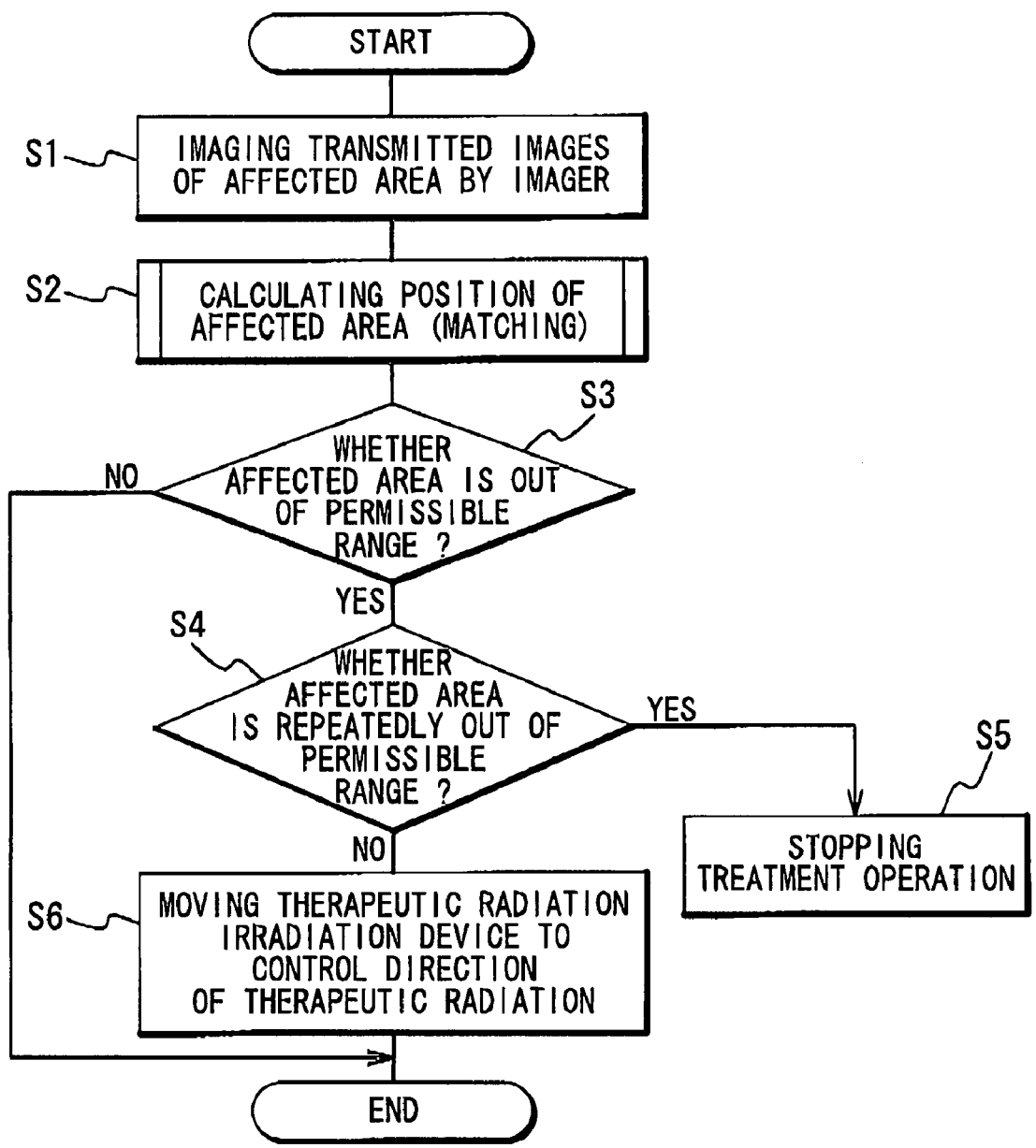
FIG. 9 is a flowchart showing a tracking operation of the embodiment.

FIG. 9 is a flowchart showing the tracking operation. The radiotherapy device control apparatus 2 irradiates the diagnostic X-ray 35 to the patient 43 by using the diagnostic X-ray source 24 and images the transmitted images of the patient 43 by using the sensor array 32. Furthermore, the radiotherapy device control apparatus 2 irradiates the diagnostic X-ray 36 to the patient 43 by using the diagnostic X-ray source 25 and images the transmitted images of the patient 43 by using the sensor array 33. Furthermore, the radiotherapy device control apparatus 2 irradiates the therapeutic radiation 23 to the patient 43 by using the therapeutic radiation irradiation device 16 and images the transmitted images of the patient 43 by using the sensor array 31 (step S1). The radiotherapy device control apparatus 2 calculates position of the affected area of the patient 43 on the basis of the transmitted images, the image templates, the width direction characteristic place template and the height direction characteristic place template calculated in the template creating operation (step S2).

The radiotherapy device control apparatus 2 determines whether or not the therapeutic radiation 23 is properly irradiated to the affected area of the patient 43 (the affected area of the patient 43 is out of a predetermined permissible range) on the basis of the calculated position (step S3). When it is considered that the affected area of the patient 43 is in a predetermined permissible range (NO at step S3), the radiotherapy device control apparatus 2 ends the tracking operation.

When it is considered that the affected area of the patient 43 is out of the predetermined permissible range (YES at step S3), the operation goes to a step S4. When it is considered that the therapeutic radiation 23 is not properly irradiated to the affected area of the patient 43 repeatedly less than a predetermined number of times (No at step S4), the radiotherapy device control apparatus 2 moves the therapeutic radiation irradiation device 16 by using the head swing device 15 so that the therapeutic radiation 23 may be irradiated to the affected area (step S6). Furthermore, the radiotherapy device control apparatus 2 calculates shape of the affected area of the patient 43 on the basis of the transmitted images imaged by the imager systems and changes shape of the irradiation field of the therapeutic radiation 23 by using the multileaf collimator 56 on the basis of the shape of the affected area so that a part of the therapeutic radiation 23 which pass an area other than the affected area may become smaller.

When it is considered that the therapeutic radiation 23 is not properly irradiated to the affected area of the patient 43 repeatedly a predetermined number of times or more (YES at step S4), the radiotherapy device control apparatus 2 stops the treatment operation (step S5). Such stop is carried out when the patient 43 moves greatly, when state of the affected area of the patient 43 has greatly changed from the time that the image templates are created, when there is an error in the treatment plan or when a problem occurs in the imager systems. This can preferably prevent an area other than the affected area of the patient 43 from being irradiated.

In the irradiating operation, the radiotherapy device control apparatus 2 irradiates the therapeutic radiation 23 with the dose shown in the treatment plan to the affected area by using the therapeutic radiation irradiation device 16.

Figure 10:
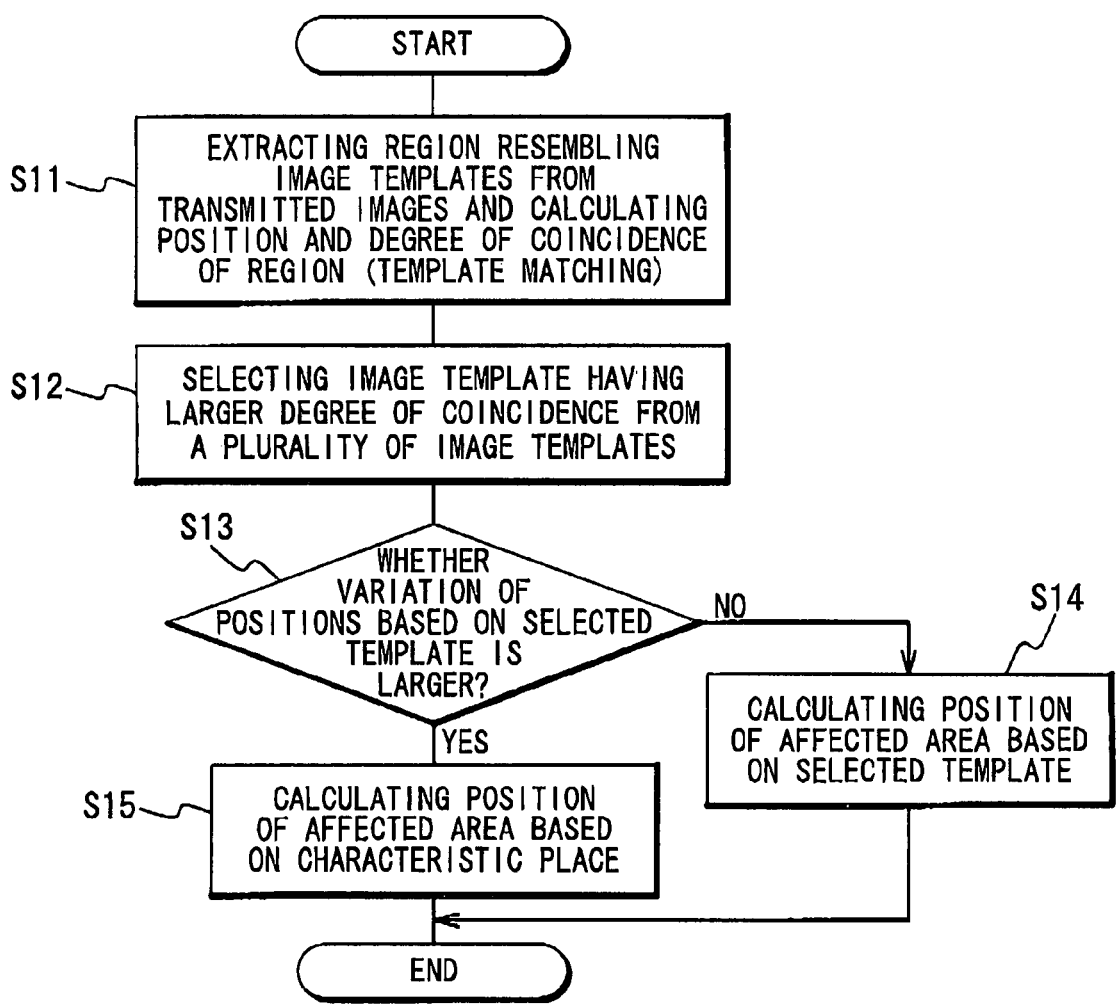
FIG. 10 is a flowchart showing a matching operation in the tracking operation of the embodiment.

FIG. 10 is a flowchart showing the step S2 in the tracking operation in detail, The radiotherapy device control apparatus 2 extracts the region which resembles the image templates most from the transmitted images imaged by the diagnostic X-ray 35 at the step S1 in the tracking operation and calculates position and degree of coincidence the of the region (step S11). The image templates created based on the plurality of transmitted images imaged by the diagnostic X-ray 35 are used and the position and degree of coincidence of the region are calculated for each of the plurality of image templates. The radiotherapy device control apparatus 2 selects the image template having larger degree of coincidence than a predetermined value from the plurality of image templates (step S12). For the transmitted images imaged by the diagnostic X-ray 36 and the transmitted images imaged by the therapeutic radiation 23, the radiotherapy device control apparatus 2 calculates position and degree of coincidence of the region and selects the image template having larger degree of coincidence than a predetermined value in the same manner.

When the selected image template is single or variation of the positions calculated based on the selected image templates is smaller than a predetermined value (NO at step S13), the radiotherapy device control apparatus 2 calculates three-dimensional position of the affected area on the basis of the position.

When the selected image templates are plural and the variation of the positions is larger than the predetermined value (YES at step S13), the radiotherapy device control apparatus 2 calculates position in the width direction of the region which resembles most from the regions extracted through template matching of the transmitted images imaged at the step S1 in the tracking operation, and also calculates position in the height direction of the region which resembles most from the extracted regions. The radiotherapy device control apparatus 2 calculates three-dimensional position of the affected area on the basis of the position in the width direction and the position in the height direction (step S15).

According to the radiation irradiation method of the present invention, it is possible to irradiate the therapeutic radiation 23 by using the therapeutic radiation irradiation device 16 to evaluate the affected area of the patient 43 using the plurality of transmitted images imaged by the sensor array 31 which are different from one another in positional relationship between the affected area of the patient 43 and the bone of the patient 43 as in the case of irradiating the diagnostic X-rays 35, 36. At this time, position of the affected area of the patient 43 can be evaluated without using either or both of the diagnostic X-rays 35, 36, which is preferable.

According to the radiation irradiation method, even when transmitted images in which the affected area of the patient is shown in close vicinity to (or overlappingly) an organs or marker which does not move together with the affected area are used, the radiotherapy system 1 can detect position of the affected area with the higher accuracy. As a result, the radiotherapy system 1 can adjust the affected area to a predetermined position with the higher accuracy and irradiate the therapeutic radiation to the affected area with the higher accuracy.

In the treatment operation, when the bone and the like have little influence on the affected area position identification of the patient 43 and position of the affected area can be satisfactorily fixed on the basis of the transmitted images by the diagnostic X-rays 35, 36, the position of the affected area is identified on the basis of the transmitted images without performing the operation shown in FIG. 9. Furthermore, to irradiate the therapeutic radiation 23 to the affected area, the therapeutic radiation irradiation device 16 can be moved by using the head swing device 15 or shape of an irradiation field of the therapeutic radiation 23 can be changed by using the multileaf collimator 56. Such affected area position identification enables three-dimensional identification of the affected area of the patient 43 and thus has a higher accuracy than the affected area position identification using the template matching.

In another embodiment of the radiotherapy device control apparatus according to the present invention, the template creating section 62 has another template creating function. The template creating section collects a plurality of three-dimensional data showing positional relationship between the affected area of the patient 43 and the organs surrounding the affected area, which are generated by the CT 5, from the CT 5. The plurality of three-dimensional data are measured at times when the positional relationship between the affected area of the patient 43 and the bone of the patient 43 is varied. The template creating section calculates DRR images on the basis of the three-dimensional data. The DRR images are two-dimensional data imaged when the X-ray is transmitted at the imaging angle shown in the treatment plan prepared by the treatment planning section 61. The template creating section displays each DRR image on the display and on the basis of information input by the user, encloses a region in the DRR image where the affected area of the patient 43 is shown with a frame. The frames are disposed so that position of the regions where the affected area of the patient 43 is shown may coincide with plurality of transmitted images. The template creating section extracts the regions enclosed with the frames from the plurality of DRR image to create a plurality of image templates. Furthermore, the template creating section creates a projective template for each image template.

Like the above-described radiotherapy device control apparatus 2, even when transmitted images in which the affected area of the patient is shown in close vicinity to (or overlappingly) an organs or marker which does not move together with the affected area are used, the radiotherapy device control apparatus can detect position of the affected area with the higher accuracy. As a result, the radiotherapy system 1 can adjust the affected area to a predetermined position with the higher accuracy and irradiate the therapeutic radiation to the affected area with the higher accuracy.

In another embodiment of the radiotherapy device control apparatus according to the present invention, the characteristic place extracting section 63 has another characteristic place extracting function and the affected area position calculating section 65 has another affected area position calculating function. The characteristic place extracting section calculates partial region characteristic place templates on the basis of the plurality of image templates calculated based on the plurality of transmitted images imaged at the same position. The affected area position calculating section calculates position of a region which resembles the partial region characteristic place templates most from the regions extracted by the template matching section 64 of the transmitted images imaged in the tracking operation.

Figure 11:
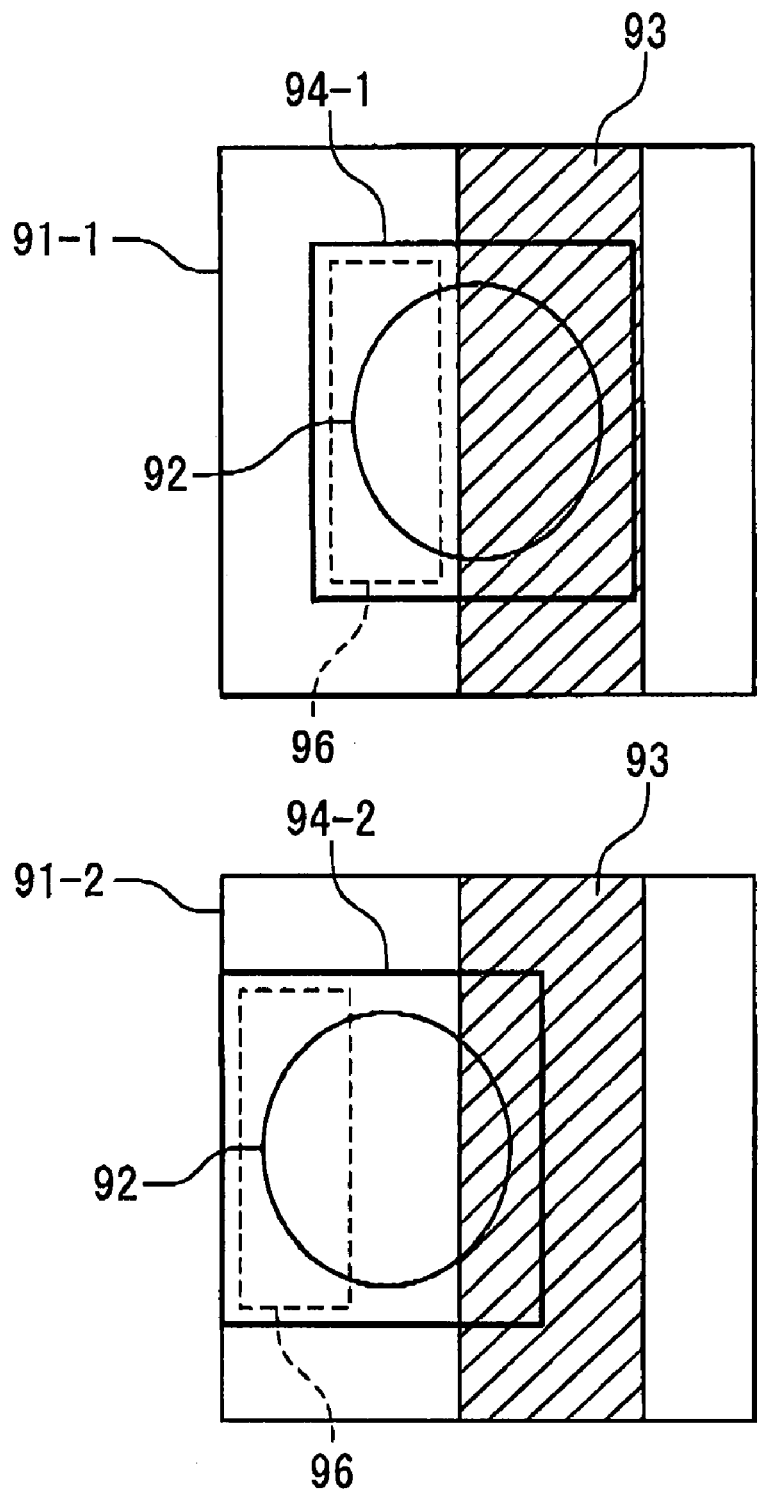
FIG. 11 is a view showing examples of common partial characteristic place templates of the embodiment.

FIG. 11 is a view showing examples of the partial region characteristic place templates. The partial region characteristic place template 96 is formed of a part of an image template 94-1 calculated based on a transmitted image 91-1. The part corresponds to a part of an image template 94-2 calculated based on a transmitted image 91-2 imaged in the same direction as the transmitted image 91-1. That is, the image in the region of the image template 94-1 corresponding to the partial region characteristic place template 96 corresponds to the image in the region of the image template 94-2 corresponding to the partial region characteristic place template 96. Furthermore, the position of the image template 94-1 corresponding to the partial region characteristic place template 96 corresponds to the position of the image template 94-2 corresponding to the partial region characteristic place template 96.

The radiotherapy device control apparatus imposes larger loads on the CPU than position identification using the width direction characteristic place templates and the height direction characteristic place templates. However, like the radiotherapy device control apparatus 2 in the above-described embodiment, even when the transmitted images in which the affected area of the patient is shown in close vicinity to (or overlappingly) an organs or marker which does not move together with the affected area are used, the radiotherapy device control apparatus can detect position of the affected area with the higher accuracy. As a result, the radiotherapy system 1 can adjust the affected area to a predetermined position with the higher accuracy and irradiate the therapeutic radiation to the affected area with the higher accuracy.

In another embodiment of the radiotherapy device control apparatus according to the present invention, the characteristic place extracting section 63 has another characteristic place extracting function and the affected area position calculating section 65 has another affected area position calculating function. The characteristic place extracting section calculates circumference characteristic place templates on the basis of the plurality of image templates calculated based on the plurality of transmitted images imaged at the same position. The circumference characteristic place templates shows circumference of figures corresponding to the affected areas in the plurality of figures shown in the image templates. The affected area position calculating section calculates position of the figure of the circumference shown in the circumference characteristic place template from the region among the transmitted images imaged in the tracking operation which are extracted by the template matching section 64 and calculates position of the affected area.

Like the radiotherapy device control apparatus 2 in the above-described embodiment, even when transmitted images in which the affected area of the patient is shown in close vicinity to (or overlappingly) the organs or the marker which does not move together with the affected area are used, the radiotherapy device control apparatus can detect position of the affected area with the higher accuracy. As a result, the radiotherapy system 1 can adjust the affected area to a predetermined position with the higher accuracy and irradiate the therapeutic radiation to the affected area with the higher accuracy.

In another embodiment of the radiotherapy device control apparatus according to the present invention, the affected area position calculating section 65 has another affected area position calculating section. The affected area position calculating section images transmitted images of the patient 43 by using the imager systems, calculates position of the whole transmitted images which substantially corresponds to the characteristic place template calculated by the characteristic place extracting section 63 and calculates position of the affected area. The characteristic place template is either of the above-described width (height) direction characteristic place template, the partial region characteristic place template or the circumference characteristic place template.

Like the radiotherapy device control apparatus 2 in the above-described embodiment, even when the transmitted images in which the affected area of the patient is shown in close vicinity to (or overlappingly) an organs or marker which does not move together with the affected area are used, the radiotherapy device control apparatus can detect position of the affected area with the higher accuracy. As a result, the radiotherapy system 1 can adjust the affected area to the predetermined position with the higher accuracy and irradiate the therapeutic radiation to the affected area with the higher accuracy.

It is apparent that the present invention is not limited to the above embodiment that may be modified and changed without departing from the scope and spirit of the invention.

The invention claimed is:

1. A radiotherapy device control apparatus for controlling a radiotherapy device, wherein the radiotherapy device includes: a therapeutic radiation irradiation device which radiates therapeutic radiation; and an imager which generates an imager image of a subject by using radiation transmitted through the subject, said radiotherapy device control apparatus comprising:

a characteristic place extracting section for creating a plurality of projective templates, each of which indicates a change in projection brightness obtained by projecting each of a plurality of image templates in one direction, wherein positional relations between an object area and a non-object area of the subject are different from each other in said plurality of image templates, and for creating characteristic place templates indicating portions common to said plurality of projective templates; and an affected area position calculating section for calculating a position of said object area by executing pattern matching on said characteristic place templates with a pattern indicating change in projection brightness obtained by projecting the imager image in one direction.

2. The radiotherapy device control apparatus according to claim 1, further comprising:

a template creating section for creating said plurality of image templates based on transmitted images imaged by using the imager.

3. The radiotherapy device control apparatus according to claim 1, further comprising:

a template creating section for creating said plurality of image templates based on three-dimensional data of the subject created by a three-dimensional imaging device provided separately with the radiotherapy device.

4. The radiotherapy device control apparatus according to claim 1, further comprising:

an irradiation position control section for judging whether a relative position of said object area with respect to the therapeutic radiation irradiation device is appropriate or not.

5. The radiotherapy device control apparatus according to claim 4, wherein said irradiation position control section moves one of the therapeutic radiation irradiation device and a couch on which the subject is arranged by using a drive device provided with the radiotherapy device such that said object area is irradiated with the therapeutic radiation.

6. The radiotherapy device control apparatus according to claim 4, wherein said irradiation position control section stops an operation of the therapeutic radiation irradiation device when judging that said relative position is not appropriate repeatedly in a predetermined number of times of said judgment, and said irradiation position control section moves the therapeutic radiation irradiation device by using a drive device provided with the radiotherapy device such that said object area is irradiated with the therapeutic radiation when judging that said relative position is appropriate within said predetermined number of times.

7. A radiotherapy device control apparatus for controlling a radiotherapy device, wherein the radiotherapy device includes: a therapeutic radiation irradiation device which radiates therapeutic radiation; and an imager which generates an imager image of a subject by using radiation transmitted through the subject, said radiotherapy control apparatus comprising:

a characteristic place extracting section for creating a plurality of projective templates, each of which indicates change in projection brightness obtained by projecting each of a plurality of image templates in one direction, wherein positional relations between an object area and a non-object area of the subject are different from each other in said plurality of image templates, and for creating characteristic place templates indicating portions common to said plurality of projective templates;

a template matching section for calculating a degree of coincidence when a pattern matching is executed on the imager image with said plurality of image templates, and for selecting a specified image template having a degree of coincidence within a predetermined range from said plurality of image templates; and an affected area position calculating section for calculating a position of said object area by executing a pattern matching on the imager image with said specified image template, when a difference between the position of said object areas in the imager image and said specified image template at said pattern matching on the imager image with said specified image template is larger than a predetermined value, and calculating the position of said object area by executing a pattern matching on said characteristic place templates with a pattern indicating change in projection brightness obtained by projecting the imager image in one direction, when said difference is equal to or smaller than said predetermined value.

8. The radiotherapy device control apparatus according to claim 7, further comprising:

a template creating section for creating said plurality of image templates based on transmitted images imaged by using the imager.

9. The radiotherapy device control apparatus according to claim 7, further comprising:

a template creating section for creating said plurality of image templates based on three-dimensional data of the subject created by a three-dimensional imaging device provided separately with the radiotherapy device.

10. The radiotherapy device control apparatus according to claim 7, further comprising:

an irradiation position control section for judging whether a relative position of said object area with respect to the therapeutic radiation irradiation device is appropriate or not.

11. The radiotherapy device control apparatus according to claim 10, wherein said irradiation position control section moves one of the therapeutic radiation irradiation device and a couch on which the subject is arranged by using a drive device provided with the radiotherapy device such that said object area is irradiated with the therapeutic radiation.

12. The radiotherapy device control apparatus according to claim 10, wherein said irradiation position control section stops an operation of the therapeutic radiation irradiation device when judging that said relative position is not appropriate repeatedly in a predetermined number of times of said judgment, and said irradiation position control section moves the therapeutic radiation irradiation device by using a drive device provided with the radiotherapy device such that said object area is irradiated with the therapeutic radiation when judging that said relative position is appropriate within said predetermined number of times.

13. A radiotherapy system comprising:

a radiotherapy device comprising:

a therapeutic radiation irradiation device which radiates therapeutic radiation, and an imager which generates an imager image of a subject by using radiation transmitted through said subject; and a radiotherapy device control apparatus for controlling said radiotherapy device, said radiotherapy device control apparatus comprising:

a characteristic place extracting section for creating a plurality of projective templates, each of which indicates change in projection brightness obtained by projecting each of a plurality of image templates in one direction, wherein positional relations between an object area and a non-object area of the subject are different from each other in said plurality of image templates, and for creating characteristic place templates indicating portions common to said plurality of projective templates, and an affected area position calculating section for calculating a position of said object area by executing a pattern matching on said characteristic place templates with a pattern indicating change in projection brightness obtained by projecting the imager image in one direction.

14. The radiotherapy system according to claim 13, wherein said radiotherapy device control apparatus further comprises:

a template creating section for creating said plurality of image templates based on transmitted images imaged by using said imager.

15. The radiotherapy system according to claim 13, wherein said radiotherapy device control apparatus further comprises:

a template creating section for creating said plurality of image templates based on three-dimensional data of the subject created by a three-dimensional imaging device provided separately with said radiotherapy device.

16. The radiotherapy system according to claim 13, wherein said radiotherapy device control apparatus further comprises:

an irradiation position control section for judging whether a relative position of said object area with respect to said therapeutic radiation irradiation device is appropriate or not.

17. The radiotherapy system according to claim 16, wherein said irradiation position control section moves one of said therapeutic radiation irradiation device and a couch on which the subject is arranged by using a drive device provided with said radiotherapy device such that said object area is irradiated with the therapeutic radiation.

18. The radiotherapy system according to claim 16, wherein said irradiation position control section stops an operation of said therapeutic radiation irradiation device when judging that said relative position is not appropriate repeatedly in a predetermined number of times of said judgment, and said irradiation position control section moves said therapeutic radiation irradiation device by using a drive device provided with said radiotherapy device such that said object area is irradiated with the therapeutic radiation when judging that said relative position is appropriate within said predetermined number of times.

19. A radiotherapy system comprising:

a radiotherapy device comprising:

a therapeutic radiation irradiation device which radiates therapeutic radiation, and an imager which generates an imager image of a subject by using radiation transmitted through said subject; and a radiotherapy device control apparatus for controlling said radiotherapy device, said radiotherapy device control apparatus comprising:

a characteristic place extracting section for creating a plurality of projective templates, each of which indicates change in projection brightness obtained by projecting each of a plurality of image templates in one direction, wherein positional relations between an object area and a non-object area of the subject are different from each other in said plurality of image templates, and for creating characteristic place templates indicating portions common to said plurality of projective templates, a template matching section for calculating a degree of coincidence when a pattern matching is executed on the imager image with said plurality of image templates, and for selecting a specified image template having a degree of coincidence within a predetermined range from said plurality of image templates, and an affected area position calculating section for calculating a position of said object area by executing a pattern matching on the imager image with said specified image template, when a difference between said position of said object areas in the imager image and said specified image template at said pattern matching on the imager image with said specified image template is larger than a predetermined value, and calculating the position of said object area by executing a pattern matching on said characteristic place templates with a pattern indicating change in projection brightness obtained by projecting the imager image in one direction, when said difference is equal to or smaller than said predetermined value.

20. The radiotherapy system according to claim 19, wherein said radiotherapy device control apparatus further comprises:

a template creating section for creating said plurality of image templates based on transmitted images imaged by using said imager.

21. The radiotherapy system according to claim 19, wherein said radiotherapy device control apparatus further comprises:

a template creating section for creating said plurality of image templates based on three-dimensional data of the subject created by a three-dimensional imaging device provided separately with said radiotherapy device.

22. The radiotherapy system according to claim 19, wherein said radiotherapy device control apparatus further comprises:

an irradiation position control section for judging whether a relative position of said subject area with respect to said therapeutic radiation irradiation device is appropriate or not.

23. The radiotherapy system according to claim 22, wherein said irradiation position control section moves one of said therapeutic radiation irradiation device and a couch on which the subject is arranged by using a drive device provided with said radiotherapy device such that said object area is irradiated with the therapeutic radiation.

24. The radiotherapy system according to claim 22, wherein said irradiation position control section stops an operation of said therapeutic radiation irradiation device when judging that said relative position is not appropriate repeatedly in a predetermined number of times of said judgment, and said irradiation position control section moves said therapeutic radiation irradiation device by using a drive device provided with said radiotherapy device such that said object area is irradiated with said therapeutic radiation when judging that said relative position is appropriate within said predetermined number of times.

25. A radiation irradiation method using a radiotherapy device, wherein the radiotherapy device includes: a therapeutic radiation irradiation device which radiates therapeutic radiation; and an imager which generates an imager image of a subject by using radiation transmitted through the subject, said radiation irradiation method comprising:
    creating a plurality of projective templates, each of which indicating change in projection brightness obtained by projecting each of a plurality of image templates in one direction, wherein positional relations between an object area and a non-object area of the subject are different from each other in said plurality of image templates, and creating characteristic place templates indicating portions common to said plurality of projective templates; and
    calculating a position of said object area by executing a pattern matching on said characteristic place templates with a pattern indicating change in projection brightness obtained by projecting the imager image in one direction.

26. The radiation irradiation method according to claim 25, further comprising:
    creating said plurality of image templates based on transmitted images imaged by using the imager.

27. The radiation irradiation method according to claim 25, further comprising:
    creating said plurality of image templates based on three-dimensional data of the subject created by a three-dimensional imaging device provided separately with the radiotherapy device.

28. The radiation irradiation method according to claim 25, further comprising:
    judging whether a relative position of said object area with respect to the therapeutic radiation irradiation device is appropriate or not.

29. The radiation irradiation method according to claim 28, wherein said judging comprises moving one of the therapeutic radiation irradiation device and a couch on which the subject is arranged by using a drive device provided with the radiotherapy device such that said object area is irradiated with the therapeutic radiation.

30. The radiation irradiation method according to claim 28, wherein said judging comprises stopping an operation of the therapeutic radiation irradiation device when judging that said relative position is not appropriate repeatedly in a predetermined number of times of said judging, and moving the therapeutic radiation irradiation device by using a drive device provided with the radiotherapy device such that said object area is irradiated with the therapeutic radiation when judging that said relative position is appropriate within said predetermined number of times.

31. A radiation irradiation method using a radiotherapy device, wherein the radiotherapy device includes: a therapeutic radiation irradiation device which radiates therapeutic radiation; and an imager which generates an imager image of a subject by using radiation transmitted through the subject, said radiation irradiation method comprising:
    creating a plurality of projective templates, each of which indicating change in projection brightness obtained by projecting each of a plurality of image templates in one direction, wherein positional relations between an object area and a non-object area of the subject are different from each other in said plurality of image templates, and creating characteristic place templates indicating portions common to said plurality of projective templates;
    calculating degree of coincidence when a pattern matching is executed on the imager mage with said plurality of image templates, and selecting a specified image template having a degree of coincidence within a predetermined range from said plurality of image templates;
    calculating a position of said object area by executing a pattern matching on the imager image with said specified image template, when a difference between said position of said object areas in the imager image and said specified image template at said pattern matching on the imager image with said specified image template is larger than a predetermined value; and
    calculating the position of said object area by executing a pattern matching on said characteristic place templates with a pattern indicating change in projection brightness obtained by projecting the imager image in one direction, when said difference is equal to or smaller than aid predetermined value.

32. The radiation irradiation method according to claim 31, further comprising:
    creating said plurality of image templates based on transmitted images imaged by using the imager.

33. The radiation irradiation method according to claim 31, further comprising:
    creating said plurality of image templates based on three-dimensional data of the subject created by a three-dimensional imaging device provided separately with the radiotherapy device.

34. The radiation irradiation method according to claim 31, further comprising:
    judging whether a relative position of said object area with respect to the therapeutic radiation irradiation device is appropriate or not.

35. The radiation irradiation method according to claim 34, wherein said judging comprises moving one of the therapeutic radiation irradiation device and a couch on which the subject is arranged by using a drive device provided with the radiotherapy device such that said object area is irradiated with the therapeutic radiation.

36. The radiation irradiation method according to claim 34, wherein said judging comprises stopping an operation of the therapeutic radiation irradiation device when judging that said relative position is not appropriate repeatedly in a predetermined number of times of said judging, and moving the therapeutic radiation irradiation device by using a drive device provided with the radiotherapy device such that said object area is irradiated with the therapeutic radiation when judging that said relative position is appropriate within said predetermined number of times.

37. A computer program product for a radiation irradiation method using a radiotherapy device including: a therapeutic radiation irradiation device which radiates therapeutic radiation; and an imager which generates an imager image of a subject by using radiation transmitted through the subject, said computer program product embodied on a computer-readable medium and comprising code that, when executed, causes a computer to perform at least the following:
    creating a plurality of projective templates, each of which indicates change in projection brightness obtained by projecting each of a plurality of image templates in one direction, wherein positional relations between an object area and a non-object area of the subject are different from each other in said plurality of image templates, and creating characteristic place templates indicating portions common to said plurality of projective templates; and calculating a position of said object area by executing a pattern matching on said characteristic place templates with a pattern indicating change in projection brightness obtained by projecting the imager image in one direction.

38. The computer program product according to claim 37, further comprising code that, when executed, causes the computer to perform at least the following:

creating said plurality of image templates based on transmitted images imaged by using the imager.

39. The computer program product according to claim 37, further comprising code that, when executed, causes the computer to perform at least the following:

creating said plurality of image templates based on three-dimensional data of the subject created by a three-dimensional imaging device provided separately with the radiotherapy device.

40. The computer program product according to claim 37, further comprising code that, when executed, causes the computer to perform at least the following:

judging whether a relative position of said object area with respect to the therapeutic radiation irradiation device is appropriate or not.

41. The computer program product according to claim 40, wherein said judging comprises moving one of the therapeutic radiation irradiation device and a couch on which the subject is arranged by using a drive device provided with the radiotherapy device such that said object area is irradiated with the therapeutic radiation.

42. The computer program product according to claim 40, wherein said judging comprises stopping an operation of the therapeutic radiation irradiation device when judging that said relative position is not appropriate repeatedly in a predetermined number of times of said judging, and moving the therapeutic radiation irradiation device by using a drive device provided with the radiotherapy device such that said object area is irradiated with the therapeutic radiation when judging that said relative position is appropriate within said predetermined number of times.

43. A computer program product for a radiation irradiation method using a radiotherapy device including: a therapeutic radiation irradiation device which radiates therapeutic radiation; and an imager which generates an imager image of a subject by using radiation transmitted through the subject, said computer program product embodied on a computer-readable medium and comprising code that, when executed, causes a computer to perform at least the following:

creating a plurality of projective templates, each of which indicates change in projection brightness obtained by projecting each of a plurality of image templates in one direction, wherein positional relations between an object area and a non-object area of the subject are different from each other in said plurality of image templates, and creating characteristic place templates indicating portions common to said plurality of projective templates;

calculating degree of coincidence when a pattern matching is executed on the imager image with said plurality of image templates, and selecting a specified image template having a degree of coincidence within a predetermined range from said plurality of image templates;

calculating a position of said object area by executing a pattern matching on the imager image with said specified image template, when a difference between said position of said object areas in the imager image and said specified image template at said pattern matching on the imager image with said specified image template is larger than a predetermined value; and calculating the position of said object area by executing a pattern matching on said characteristic place templates with a pattern indicating change in projection brightness obtained by projecting the imager image in one direction, when said difference is equal to or smaller than said predetermined value.

44. The computer program product according to claim 43, further comprising code that, when executed, causes the computer to perform at least the following:

creating said plurality of image templates based on transmitted images imaged by using the imager.

45. The computer program product according to claim 43, further comprising code that, when executed, causes the computer to perform at least the following:

creating said plurality of image templates based on three-dimensional data of the subject created by a three-dimensional imaging device provided separately with the radiotherapy device.

46. The computer program product according to claim 43, further comprising code that, when executed, causes the computer to perform at least the following:

judging whether a relative position of said object area with respect to the therapeutic radiation irradiation device is appropriate or not.

47. The computer program product according to claim 46, wherein said judging comprises moving one of the therapeutic radiation irradiation device and a couch on which the subject is arranged by using a drive device provided with the radiotherapy device such that said object area is irradiated with the therapeutic radiation.

48. The computer program product according to claim 46, wherein said judging comprises stopping an operation of the therapeutic radiation irradiation device when judging that said relative position is not appropriate repeatedly in a predetermined number of times of said judging, and moving the therapeutic radiation irradiation device by using a drive device provided with the radiotherapy device such that said object area is irradiated with the therapeutic radiation when judging that said relative position is appropriate within said predetermined number of times.

* * * * *